Figure 1:
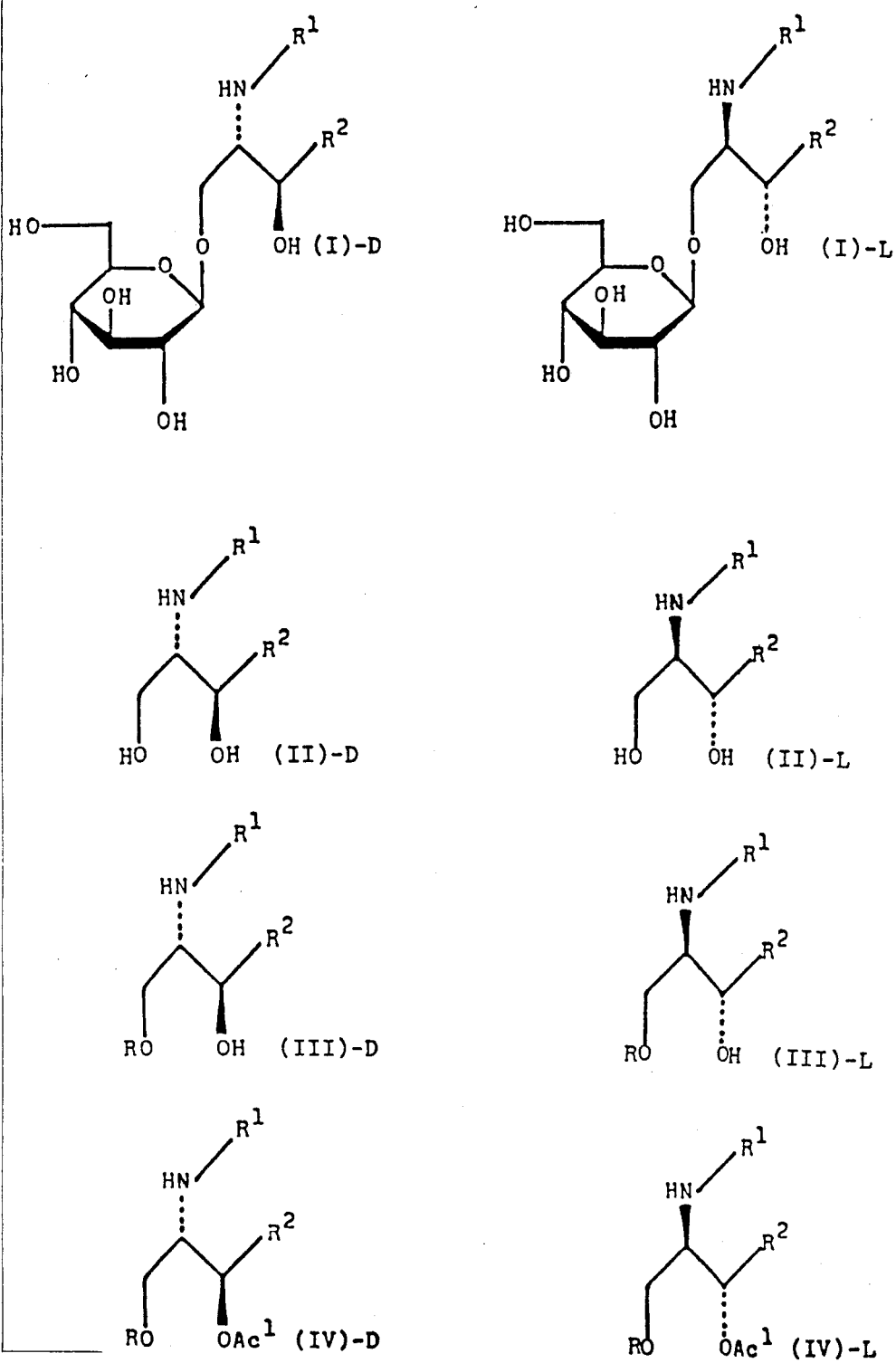
Figures 1, 2:
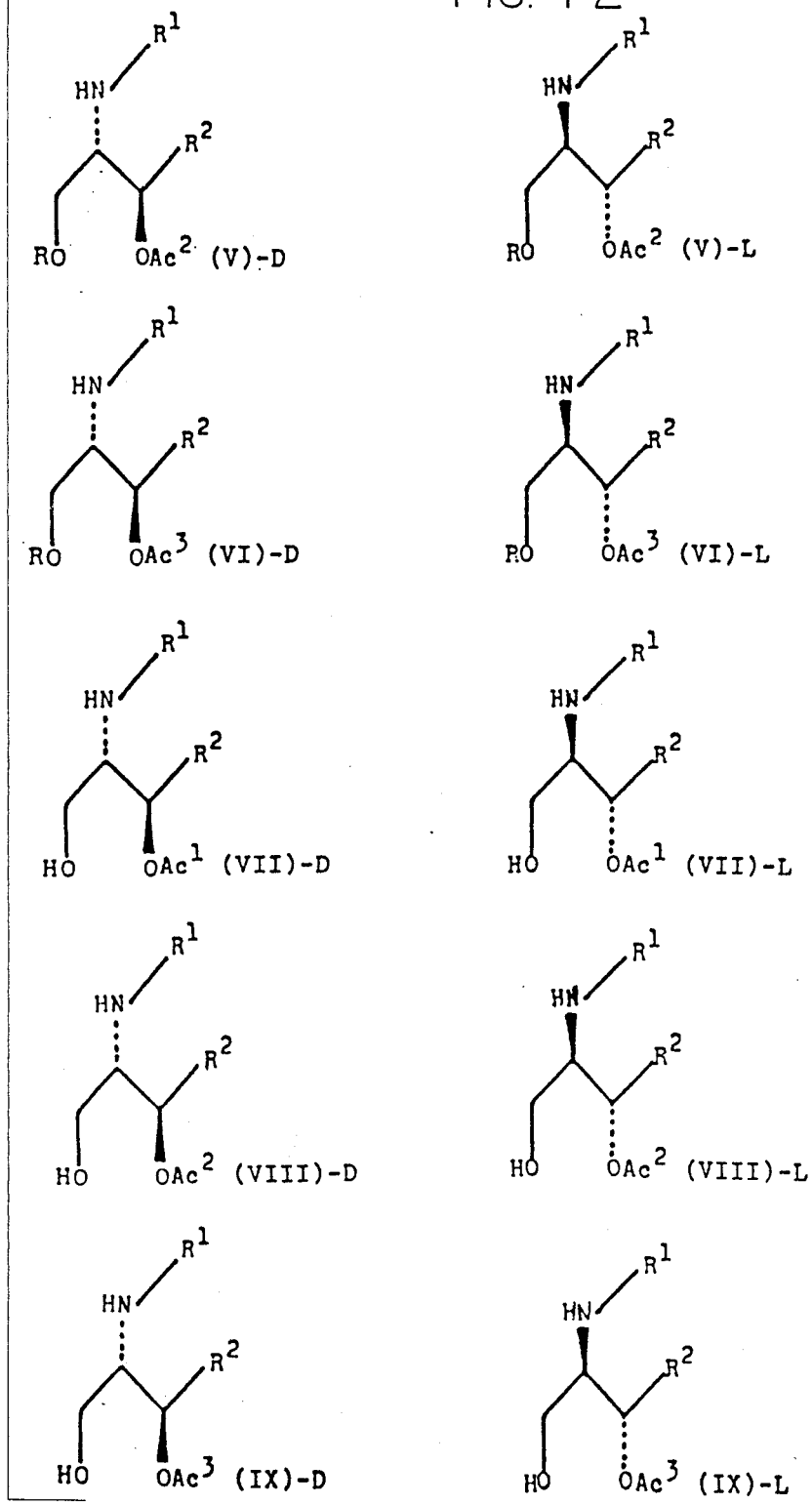
Figures 1, 2, 3:
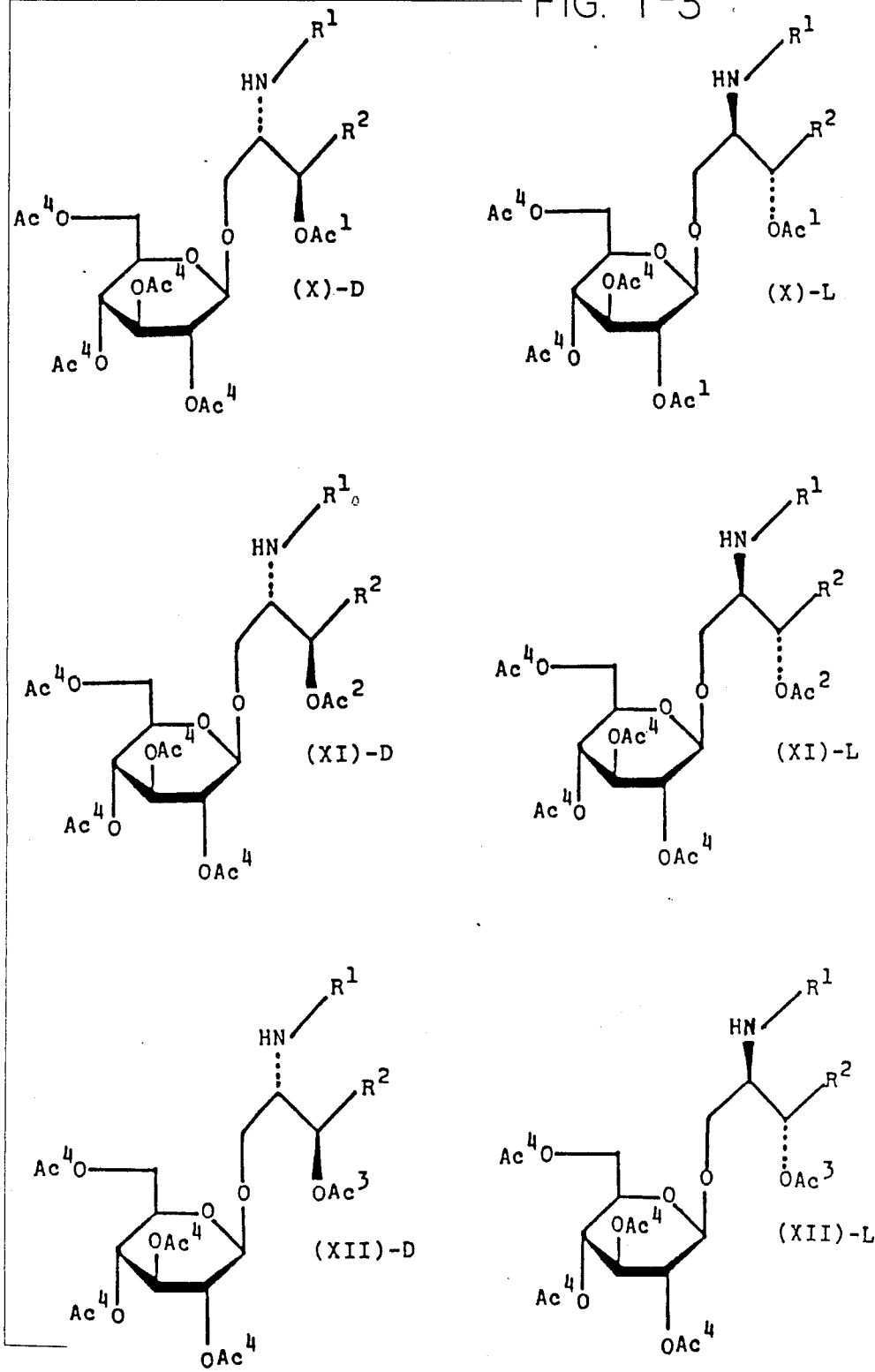

United States Patent [19]

Tschannen et al.

[11] Patent Number: 4,952,683

[45] Date of Patent: Aug. 28, 1990

[54] PROCESS FOR THE PREPARATION OF SPHINGOSINE DERIVATIVES

[75] Inventors: Roland Tschannen, Basel; Wolfgang Fraefel, Grolley, both of Switzerland; Richard R. Schmidt, Konstanz, Fed. Rep. of Germany; Rudolf Klager, Eutingen, Fed. Rep. of Germany; Peter Zimmermann, Villingen, Fed. Rep. of Germany

[73] Assignee: Solco Basel AG, Switzerland

[21] Appl. No.: 137,957

[22] Filed: Dec. 24, 1987

Related U.S. Application Data

[63] Continuation of Ser. No. 676,061, Nov. 29, 1984, abandoned.

[30] Foreign Application Priority Data

Dec. 5, 1983 [CH] Switzerland .......................... 6493/83
Sep. 28, 1984 [CH] Switzerland .......................... 4671/84

[51] Int. Cl.$^5$ .............................................. C07H 5/06
[52] U.S. Cl. .................................... 536/186; 536/17.9; 536/18.5
[58] Field of Search .................. 536/4.1, 17.2, 17.9, 536/18.6, 18.5

[56] References Cited

U.S. PATENT DOCUMENTS 4,042,538 8/1977 Lucas .................................. 536/4.1
4,362,720 12/1982 Lemieux et al. ................... 536/17.2

OTHER PUBLICATIONS

Jungerman et al., *Biochemie* pp. 448, 1980, published by Springer-Verlag Berlin, Heidelburg, N.Y.
Lehringer, *Biochemie* pp. 177–180, 1975, published by Verlag-Chemie.
Schmidt et al., Chemical Abstracts, vol. 96, (1982), No. 123 141m.

*Primary Examiner*—Johnnie R. Brown
*Assistant Examiner*—Elli Peselev
*Attorney, Agent, or Firm*—Wenderoth, Lind & Ponack

[57] ABSTRACT

New compounds of the formula (I)-D and (I)-L as shown in the sheet of formulae are described, for example D- and L-erythro-1-($\beta$-D-glycopyranosyloxy)-3-hydroxy-2-palmitoylamino-4-trans-octadecene, which exert actions promoting wound healing and cell and tissue regeneration, and can be used therapeutically for the treatment of wounds of any cause. They are prepared in good yield and in a stereochemically homogeneous form from ceramides of the formula (II)-D and/or (II)-L. The process comprises the protection of the 1-hydroxyl group, esterification of the 3-hydroxyl group, elimination of the 1-hydroxyl protective group, reaction with the trifluoroacetimidate or trichloroacetimidate of a 2,3,4,6-tetraacylated D-glucose and elimination of the O-acyl groups. When a D,L-ceramide (II) is used, the esterification of the 3-hydroxyl group is carried out by an optically active acid followed by separation into the diastereomers, or separation into the diastereomers is carried out after the reaction with the D-glucose derivative.

23 Claims, 3 Drawing Sheets

PROCESS FOR THE PREPARATION OF SPHINGOSINE DERIVATIVES

This is a continuation of co-pending application Ser. No. 06/676,061 filed on Nov. 29, 1984 now abandoned.

Of the lipids hitherto known to occur in the human body, two groups are distinguished: the humoral lipids which are not structurally bound, and those which are constituents of cell structures.

Examples of humoral lipids which exert a biological function in higher organisms include steroid hormones and prostaglandins. The latter are involved in inflammatory reactions of tissues.

The lipids which are structurally bound are of importance, apart from their energy-storage function, particularly in the cell structures which divide various compartments of the cells. There is increasing recognition of how individual lipids can affect and control the transmission of signals through these membranes, for example by changing the membrane fluidity (rate of lateral diffusion of the membrane lipids). During the course of a cycle of division of the cells there are continuous changes in the composition of the membranes and thus in their physical properties. The known components of the membrane are, in particular phospholipids, sterines and glycophingolipids.

The glycosphingolipids are derivatives of ceramides which are composed of an aminodiol, such as the $C_{18}$ sphingosine or $C_{20}$ sphingosine:

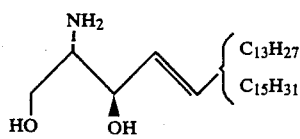

and a long-chain fatty acid radical (RCO—), and they correspond to the following general formula:

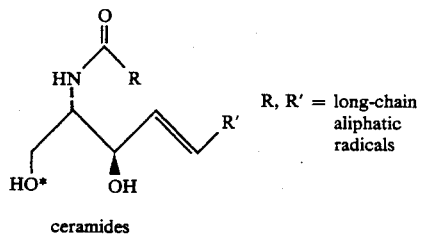

ceramides

R, R' = long-chain aliphatic radicals

A carbohydrate moiety which can be composed of 1 to 20 or even more sugar units is bound to the hydroxyl group indicated by * in the ceramides.

The glycosphingolipids fall into two main classes depending on the nature of the carbohydrate moiety. When the ceramide is linked to one or more monosaccharides they are neutral glycosphingolipids—also called cerebrosides, while linkage with an oligosaccharide which is substituted by acylneuraminic acids (also called sialic acids) results in the acid glycophingolipids—also called gangliosides. The latter are attributed with receptor functions, for example for viruses and toxins; they are also said to have a neuro-regenerative effect.

This state of the art is illustrated by, in particular, the following papers:

K. Jungermann and H. Möhler: Biochemie (Biochemistry) published by Springer, Berlin, Heidelberg, New York, 1980, 448–452;

S. Hakomori, Annual Review of Biochemistry 52 (1981), 733–764.

In the true cerebrosides originating from the brain, the fatty acid component usually comprises a $C_{24}$ carboxylic acid which may carry a hydroxyl group in the α-position or a double bond. For example, lignoceric acid $C_{24}H_{48}O_2$ is found in kerasin, nervonic acid $C_{24}H_{46}O_2$ is found in nervone, cerebronic acid $C_{24}H_{48}O_3$ is found in cerebrone or phrenosin, and hydroxynervonic acid $C_{24}H_{26}O_3$ is found in hydroxynervone. In these and in most cerebrosides, the carbohydrate moiety comprises 1 mol of galactose.

Recently, other neutral glycophingolipids have been discovered, and these have a fatty acid component with a shorter aliphatic chain and have a carbohydrate moiety composed of several sugar units. However, these compounds have not been found in the brain but in other organs, for example in the intestines, in the spleen, in the liver and in the erythrocytes, for which reason the name cerebrosides should no longer be used or should be used only for the group mentioned above.

Surprisingly, a new group of neutral glycosphingolipids has now been found, and these are distinguished from the abovementioned compounds which are already known by another fatty acid component and/or another carbohydrate moiety, namely 1 mol of D-glucose. This new chemical structure is reflected in an action promoting wound healing and cell and tissue regeneration, which has likewise hitherto been unknown for glycophingolipids.

These compounds are represented by formula (I)-D and (I)-L on the attached sheet of formulae; as is clear from the formulae, they have the erythro configuration.

In the case of compounds of the formula (I)-D, they can be regarded as intermediates in the biosynthesis or in the metabolism of naturally occurring (in organs and body fluids of mammals) higher glycosphingolipids, such as the gangliosides, which have a carbohydrate moiety composed of several sugar units. In contrast, the compounds of the formula (I)-L have no place in nature, nor can they be regarded as part formulae or precursors of more complex compounds.

In the formulae (I)-D and (I)-L:

$R^1$ denotes the acyl radical of a fatty acid having 14 to 24 carbon atoms or the corresponding acyl radicals having a hydroxyl group in the α-position or having 1 or 2 double bonds in the cis configuration, and $R^2$ denotes the pentadecanyl or heptadecanyl radical or the corresponding $C_{15}$ and $C_{17}$ radicals having 1, 2 or 3 double bonds, one of which in each case being located in the 1,2-position and having the trans configuration, the other, or others, when present, having the cis configuration.

The chemical structure is homogeneous in the carbohydrate moiety; nevertheless, there is a remarkable variety of glycosphingolipids which promote wound healing. However, in this context it should be noted that this variety arises merely by variation in the lipid moiety. This appears biologically rational, since the biological activity is principally determined by the carbohydrate moiety of the molecule, which is directed outwards from a membrane. The fluidity of membranes is affected, for example by glucosphingolipids, by the possibility of the amide proton of the ceramide interacting with the phosphate groups of phospholipids and thus conferring more stability on a lipid membrane than can arise merely by a phospholipid/steroid interaction.

In vivo, the compounds display a promoting action on cell and tissue regeneration. This action can also be detected in vitro using cell cultures. Thus, if the rate of division in a cell culture, for example a culture of fibroblasts, is first artificially reduced by exposure to an injurious agent, and if the culture is then treated with the compounds, then the rate of division is returned within a short time to a normal figure which is compartable or identical to that in a healthy, undamaged culture. In contrast, the same treatment of a parallel but healthy cell culture brings about no change in the rate of division. Thus, in this instance, there is not merely a mitotic action, for example.

As a result of the described promoting action on the regeneration mechanisms of damaged cells, the compounds are suitable for therapeutic use for wounds of any cause, in particular wounds which are healing poorly or slowly, or ulcerations. And in fact, especially when applied topically to wounds, such as ulcus cruris, ulcers of the gastrointestinal tract, in particular gastric ulcer and duodenal ulcer, diabetic gangrene, radiation damage, burns and skin transplants, they lead to the formation of healthy new tissue which has a good blood supply, without upsetting scars.

As a result of their high therapeutic efficacy, the sphingosine derivatives of the formula (I)-D are very generally preferred.

On the other hand, because of their higher specific activity (activity per microgram of the compound) those sphingosine derivatives of the formula (I)-D and (I)-L in which $R^1$ denotes the acyl radical of a fatty acid having 14 to 20 carbon atoms or the corresponding acyl radicals having a hydroxyl group in the α-position or having 1 or 2 double bonds in the cis configuration, but $R^2$ retains the meaning indicated above, are likewise preferred.

Particularly preferred sphingosine derivatives are those of the smaller group which is represented by the formula (I)-D in which $R^1$ denotes the acyl radical of a fatty acid, an α-hydroxy fatty acid or a fatty acid with 1 or 2 cis-olefinic insaturations, said acids having 14 to 20 carbon atoms, and $R^2$ retains the meaning indicated above.

Examples of the compounds according to the invention are, inter alia:

D- and L-erythro-1-(β-D-glucopyranosyloxy)-3-hydroxy-2-myristoylamino-4-trans-octadecene and the corresponding -4-trans-eicosenes;

D- and L-erythro-1-(β-D-glucopyranosyloxy)-3-hydroxy-2-palmitoylamino-4-trans-octadecene and the corresponding -4-trans-eicosenes;

D- and L-erythro-1-(β-D-glucopyranosyloxy)-3-hydroxy-2-stearoylamino-4-trans-octadecene and the corresponding -4-trans-eicosenes;

D- and L-erythro-1-(β-D-glucopyranosyloxy)-3-hydroxy-2-(9-cis-octadeceneoylamino)-4-trans-octadecene and the corresponding -4-trans-eicosenes;

D- and L-erythro-1-(β-D-glucopyranosyloxy)-3-hydroxy-2-(cis,cis-9,12-octadecadienoylamino)-4-trans-octadecene and the corresponding -4-trans-eicosenes;

D- and L-erythro-1-(β-D-glucopyranosyloxy)-3-hydroxy-2-eicosanoylamino-4-trans-octadecene and the corresponding -4-trans-eicosenes;

D- and L-erythro-1-(β-D-glucopyranosyloxy)-3-hydroxy-2-docosanoylamino-4-trans-octadecene and the corresponding -4-trans-eicosenes;

D- and L-erythro-1-(β-D-glucopyranosyloxy)-3-hydroxy-2-tetracosanoylamino-4-trans-octadecene and the corresponding -4-trans-eicosenes.

According to the invention, the sphingosine derivatives of the formula (I)-D or (I)-L are prepared in the pure state and with satisfactory yields by total synthesis. The process is outstandingly suitable for use on the industrial scale and it makes the preparation of the compounds independent of any natural source.

The process comprises reacting an optically active compound of the formula (II)-D or (II)-L

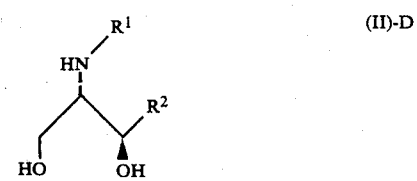

(II)-D

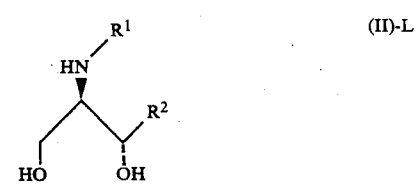

(II)-L in which $R^1$ and $R^2$ have the meaning indicated above, or the corresponding racemate, with an organic reagent which is able selectively to react with a primary hydroxyl group, with the formation of compounds of the formula (III)

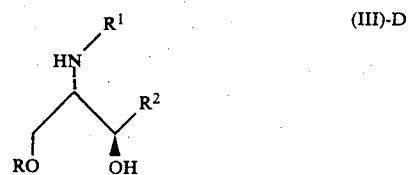

(III)-D

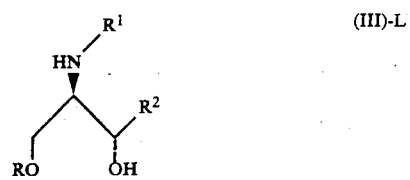

(III)-L in which R denotes a hydroxyl protective group, (A) esterifying the compound of the formula (III) with an organic carboxylic acid with the formation of a compound of the formula (IV)

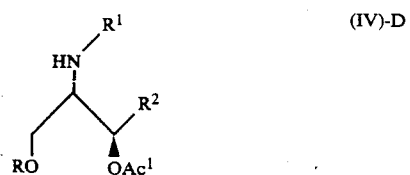

(IV)-D

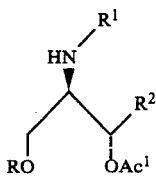

(IV)-L

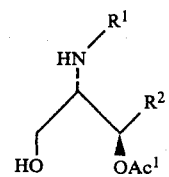

(VII)-D in which Ac¹ denotes the acyl radical of an organic carboxylic acid, or (B) when a racemate is used as the starting material, esterifying the compound of the formula (III) with an optically active organic acid, and separating into the diastereomers the resulting mixture of diastereomeric compounds of the formula (V) in which Ac² denotes the acyl radical of an optically active organic acid or (C) following variant (B), deacylating the individual diastereomers of the formula (V)

(VII)-L (VIII)

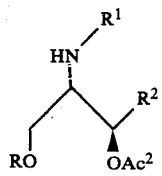

(V)-D

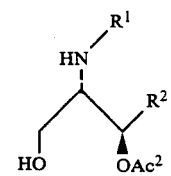

(VIII)-D

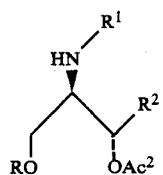

(V)-L

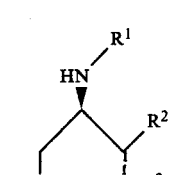

(VIII)-L and esterifying with an organic carboxylic acid with the formation of enantiomeric compounds of the formula (VI)

or (IX)

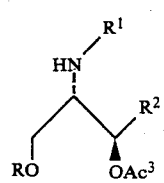

(VI)-D

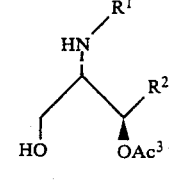

(IX)-D

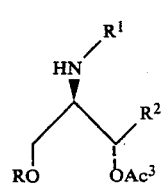

(VI)-L

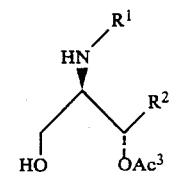

(IX)-L in which Ac³ denotes the acyl radical of an organic carboxylic acid, removing the hydroxyl protective group R from the compounds of the formula (IV) obtained in variant (A) or the diastereomers of the formula (V) obtained in variant (B) or the enantiomers of the formula (VI) obtained in variant (C) with the formation of corresponding compounds of the formula (VII), respectively, reacting the compound of the formula (VII), (VIII) or (IX) respectively with the O-trifluoroacetimidate or O-trichloroacetimidate of a D-glucose whose hydroxyl groups in the 2,3,4 and 6 positions are protected by acyl radicals Ac⁴, with the formation of compounds of the corresponding formula (X),

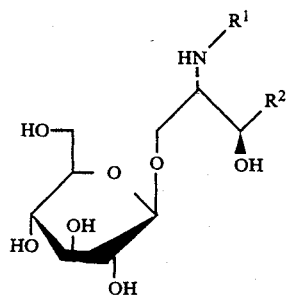
(I)-D

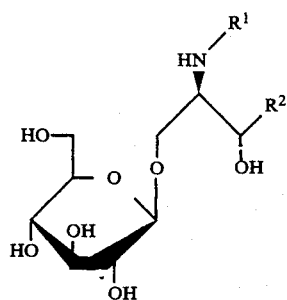
(I)-L

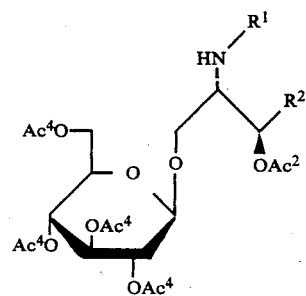
(XI)

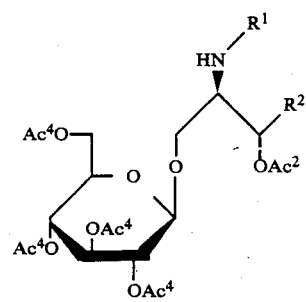
(XI)-D

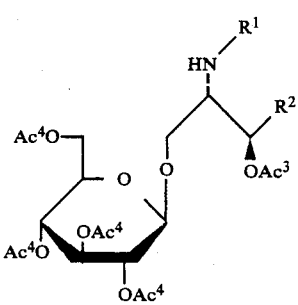
(XI)-L or (XII),

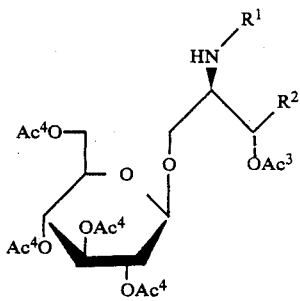
(XII)-D

-continued (XII)-L respectively, separating, if a racemate is used as starting material for variant (A), into the diastereomers the compound of the formula (X), and eliminating simultaneously the acyl groups $Ac^1$, $Ac^2$, $Ac^3$ and $Ac^4$ from the compounds of the formula (X), (XI) or (XII), in each case compounds of the D- or L-series being produced from compounds of the D- or L-series respectively.

The starting materials for the process are ceramides of the formula (II)-D and/or (II)-L; thus the process can be applied both to one of the optically active compounds and to the corresponding racemate. If a racemate is used as the starting material, then a separation into diastereomers or enantiomers is carried out at a particular stage in the process so that, in each case, the pure and stereochemically homogeneous compounds of the formula (I)-D or (I)-L are obtained as the final product.

The ceramides of the formula (II)-D or (II)-L or their racemate can in turn be prepared from corresponding $C_{18}$ or $C_{20}$ sphingosines by N-acylation using a fatty acid of the formula $R^1$-OH, in which $R^1$ has the meaning indicated above, or a reactive functional derivative of it.

Examples of the fatty acid $R^1OH$ are myristic acid, palmitic acid, stearic acid, oleic acid (cis-9-octadeceneoic acid), linoleic acid (cis,cis-9,12-octadecadieneoic acid), arachidic acid (eicosanoic acid), behenic acid (docosanoic acid) or, at the upper limit for the meaning indicated for $R^1$, tetracosanoic acid (lignoceric acid), cis-15-tetracosenoic acid (nervonic acid), 2-hydroxytetracosanoic acid (cerebronic acid), 2-hydroxy-15-tetracosenoic acid (hydroxynervonic acid) or the 2-hydroxy-17-tetracosenoic acid which is isomeric with the latter.

The acylation with the fatty acid $R^1$—OH can be brought by the process of D. Shapiro and coworkers (J.Am.Chem.Soc. 81, 4360 (1959); a particularly productive procedure has been developed for this and is described in the experimental part.

The sphingosines on which the naturally occurring glycosphingolipids, cerebrosides and gangliosides are based have the erythro configuration and belong to the D series. The process according to the invention now makes it possible to convert even racemic sphingosines into the final products of the formula (I)-D and (I)-L. This is of particular importance because the known syntheses of the D-sphingosines take place via numerous process steps, some of which are difficult, while a recent straight-forward synthesis by R. R. Schmidt and R. Kläger (Angew. Chem. 94, 215–216 (1982); Angew.-Chem.Int.Ed.Engl. 21, 210–211 (1982); Angew.Chem.-Suppl. 1982, 393–397) provides the racemic sphingosines in good yield.

The process is described in more detail below.

The protection of the primary hydroxyl group of the ceramides (II)-D and/or (II)-L should be carried out with reagents which in the presence of a primary and a secondary hydroxyl group react selectively with the former. Particularly suitable protective groups R are those which have large spatial demands, such as the tert.-butyl, triphenylmethyl (trityl), trichloroacetyl, trimethylsilyl, tert.-butyldimethylsilyl or tert.-butyldiphenylsilyl groups. The triphenylmethyl, monomethoxy-triphenylmethyl, tert.-butyldimentylsilyl and tert.-butyldiphenylsilyl groups are preferred.

The introduction of the protective group R is carried out by the known methods of organic chemistry appropriate for the type of protective group selected. For example, the triphenylmethyl group can be introduced by treating the ceramide with an appropriate halide, such as triphenylchloromethane or triphenylbromomethane. It is also advantageous with the tert.-butyldimethylsilyl and tert.-butyldiphenylsilyl groups to use the corresponding halide, preferably the chloride or the bromide.

According to a first process variant (A), the ceramide of the formula (III)-D and/or (III)-L, which is protected in the 1-position, is now esterified in the 3-position using an organic carboxylic acid of the formula $Ac^1OH$, or a reactive functional derivative of it, to give compounds of the formula (IV)-D and/or (IV)-L. Aliphatic and aromatic carboxylic acids are particularly suitable for this purpose; a monocyclic aromatic carboxylic acid, such as benzoic acid or a substituted benzoic acid, is preferably used. The same carboxylic acids are likewise suitable or are likewise preferred for the esterification with the acid of the formula $Ac^3OH$ dealt with below.

The esterification, whether with the carboxylic acid $Ac^1OH$ or $Ac^3OH$ or with the optically active organic acid $Ac^2OH$, can be carried out by the methods described in "Ullmanns Encyklopädie der technischen Chemie" (Ullmans encyclopedia of industrial chemistry), 4th edition, volume 11, pages 91 et seq., Verlag Chemie, Weinheim FGR (1976). It is advantageously carried out using a carbonyl halide in the presence of a tertiary organic base, such as triethylamine, pyridine or dimethylaniline, in an anhydrous organic solvent, such as benzene, toluene, tetrahydrofuran, diethyl ether or dichloromethane.

According to a second process variant (B), the ceramide of the formula (III), which is protected in the 1-position, is esterified in the 3-position using a simple optically active organic carboxylic acid $Ac^2OH$, or a reactive functional derivative of it, to give compounds of the formula (V). Suitable for this purpose are tartaric acid, dibenzoyltartaric acid, mandelic acid, O-acetylmandelic acid, camphoric acid, camphorsulfonic acid or bromocamphorsulfonic acid etc.; O-acetylmandelic acid is preferred. The esterification is advantageously carried out using a carbonyl halide in the presence of a tertiary organic base, such as pyridine, in an anhydrous organic solvent, such as benzene, toluene, tetrahydrofuran, diethyl ether or dichloromethane.

This is followed by separation of the mixture of diastereomeric compounds of the formula (V) by chromatography, preferably on silica gel, or by fractional crystallization.

According to a third process variant (C), the diastereomers of the formula (V) obtained by (B) are converted, by base-catalyzed elimination of the 3-O-acyl group ($Ac^2$), preferably in sodium methanolate/methanol, into the optical antipodes. These are then each esterified with a simple organic carboxylic acid of the formula $Ac^3OH$, or a reactive derivative of it, to give compounds of the formula (VI). Simple aromatic and aliphatic carboxylic acids are suitable for this purpose. An aromatic carboxylic acid, for example benzoic acid or a substituted benzoic acid, is preferably used.

The compounds (IV), (V), and (VI) obtained by variants (A), (B) and (C) are subjected to acid hydrolysis to eliminate the protective group in the 1-position (trityl protective groups, silyl protective groups), and thus the compounds (VII), (VIII) and (IX) are obtained.

The compounds (VII), (VIII) and (IX) are reacted with the O-trichloroacetimidate or O-trifluoroacetimidate of a D-glucose whose hydroxyl groups, apart from that on the 1-position, are protected by acyl radicals $Ac^4$, with the formation of compound of the formula (X), (XI) and (XII). In the case of the compound (X), the separation into the diastereomers is carried out, and the acyl groups $Ac^1$, $Ac^2$, $Ac^3$ and $Ac^4$ are eliminated simultaneously by base catalysis, preferably in sodium methanolate/methanol, from the compounds (X), (XI) and (XII).

DESCRIPTION OF THE PHARMACOLOGICAL TESTS

Test 1

Rats are anesthetized and their fur is removed. Bilateral burns are caused on the trunk by placing a metal disk of diameter 2 cm and temperature 270° C. flat on it for 17 seconds. The glucosphingolipids are incorporated in a gel base, and this is smeared on the wound twice a day. The time until the wounds have finally healed is measured. Gels which contain the glucosphingolipids result in a shortening of the healing time by up to 21% compared with the control group.

Test 2

Minipigs are each given four dorsal burns as described in Test 1 and four circular wounds with a diameter of 2.5 cm are caused using a hollow cylindrical borer. The active compounds are incorporated in a gel base and the wounds are smeared with the gel twice a day. The time until healing is complete is recorded. The time until is complete is reduced by up to 18% by the glucosphingolipids.

Test 3

Burns are caused to minipigs as described in Test 1. After 6, 12, 18 and 22 days of daily treatment of the wounds, animals are removed from the treatment group and sacrificed under anesthesia. The wounds are dissected out, divided in two and fixed in 4% buffered formalin. These pieces of tissue are converted into 4 μm thick histological paraffin sections. The following parameters are determined quantitatively:
1. Length of the wound surface which has undergone epithelization
2. Length of the wound surface which has not undergone epithelization
3. Length of the basal layer of the epidermis
4. Area of the regenerated epidermis
5. Area of hair follicles and sebaceous glands.

Evaluation of the parameters shows that the animals treated with the gel containing glucosphingolipids have a longer wound surface which has undergone epithelization and a shorter wound surface which has not undergone epithelization than the animals treated with a gel base containing no active compound.

Test 4

Circular wounds 1 cm wide and 5 mm deep are caused in anesthetized rats. Hollow cylindrical viscose/cellulose sponges are placed in these wound holes. Each day, 100 μl of a glucosphingolipid-containing solution with a content of 0.1 to 15 μg/ml glucosphingolipids is injected into the inner recess of the hollow cylinder. 16 and 24 days after implantation the sponges are removed and investigated for the content of hemoglobin, deoxyribonucleic acid and hydroxyproline. The wounds which had been treated with the glucosphingolipids have a significantly higher content of hemoglobin, DNA and hydroxyproline in the sponges than do those of the control animals.

Test 5

Fibroblast cell cultures which have grown in a nutrient medium which is buffered at pH 7.2 with bicarbonate and an atmosphere containing $CO_2$ are exposed to a new nutrient medium which contains no bicarbonate and which is exposed to the normal atmosphere, the pH being stabilized at 7.2 by addition of a suitable non-toxic buffer, such as 2-[4-(2-hydroxyethyl)-1-piperazinyl]ethanesulfonic acid/NaOH solution (HEPES). Cells which have no glucosphingolipid available in the nutrient medium virtually stop growing, while cells in the medium containing active compound rapidly recover and attain the same growth rate as control cultures in a medium containing bicarbonate. The growth rate is measured, for example after action of the glucosphingolipid for 3 days, by offering the cells $^3$H-thymidine for 5 hours. The cells are then disrupted by osmotic shock and the DNA is retained on a diethylaminoethyl filter paper. The radioactivity on this filter is measured.

The following examples illustrate preferred embodiments of the invention.

$^1$H NMR spectra were recorded using the WM 250 Cryospec 250 MHz apparatus supplied by Bruker, Spectrospin, Industriestrasse 26, CH-8117 Fällanden/Zürich. The shifts are relative to tetramethylsilane (TMS) as internal standard and are reported in ppm.

The reported melting points were determined in a copper block and are uncorrected.

Silica gel plates supplied by E. Merck AG, Darmstatt (FRG) were used for analytical thin-layer chromatography (TLC). When the substances were UV inactive, the thin-layer chromatograms were sprayed with 15% sulfuric acid and heated at 120° C.

Preparative column chromatography was carried out with silica gel, 0.062-0.200 mm, supplied by Merck. Packed columns according to D. Flockerzi, diploma thesis, University of Stuttgart (1978), with silica gel "LiChroprep Si 60, 15-25" were used for medium-pressure chromatography.

The yields have been reported at the purification stage at which no impurities were detectable by NMR spectroscopy or thin-layer chromatography.

PREPARATION OF THE STARTING MATERIALS

(a) Tetradecanal 32.3 g (150 mmol) of pyridinium chlorochromate are suspended in 200 ml of anhydrous methylene chloride at room temperature, with vigorous stirring, and a solution of 21.4 g (100 mmol) of tetradecanol in 20 ml of anhydrous methylene chloride is added. This results in the reaction mixture boiling. The reaction is complete after 1½ hours. The solution is decanted off from the solid which is washed with about 200 ml of dry diethyl ether. After filtration and evaporation of the solvent, chromatography is carried out on silica gel using petroleum ether (boiling point 35°-80° C.)/ethyl acetate 9:1. Yield: 18 g (84%).

(b) Hexadecanal 21.5 g (100 mmol) of pyridinium chlorochromate are suspended in 200 ml of anhydrous dichloromethane. 16 g (66 mmol) of hexadecanol in 50 ml of anhydrous dichloromethane are added dropwise. After 2 hours, the mixture is diluted with 300 ml of anhydrous ether, and the solution is decanted off from the black residue. The residue is washed three times with about 50 ml of anhydrous ether. The organic phases are combined and the ether is evaporated off to dryness. The residue is chromatographed on silica gel using petroleum ether/ethyl acetate 9:1. Yield: 15 g (95%), melting point 33°-34° C.

(c) Formylmethylenetriphenylphosphorane

The compound is prepared by the process in J. Chem. Soc. 1961, 1266-1272.

(d) 2-Trans-hexadecenal 100 g (0.47 mol) of tetradecenal and 173 g (0.56 mol) of formylmethylenetriphenylphosphorane in 1 liter of anhydrous chloroform are heated to boiling for 12 hours. After cooling, the mixture is evaporated and chromatographed on a short silica gel column using petroleum ether (boiling point 35°-80° C.)/ethyl acetate 9:1 in order to remove the triphenylphosphine oxide. The product is then distilled under high vacuum. The compound provides to be identical to that in Hoppe-Seyler's Z. Physiol. Chem. 354, 1626-1632 (1973). Yield: 77 g (69%).

$R_F = 0.5$, petroleum ether (boiling point 35°-80° C./ethyl acetate 9:1; UV: blue coloration with anisaldehyde reagent (0.5 ml anisaldehyde, 50 ml glacial acetic acid, 1 ml $H_2SO_4$); boiling point ($10^{-3}$ Torr): 115° C.

(e) 2-Trans-octadecenal 12 g (50 mmol) of hexadecenal and 15.2 g (50 mmol) of formylmethylenetriphenylphosphorane in 250 ml of anhydrous toluene are boiled under reflux for 8 hours. The mixture is evaporated to dryness. The residue is extracted five times with 100 ml of ether. The extract is evaporated to dryness and chromatographed on silica gel using toluene. Yield: 8.2 g (62%). Melting point: 35° C.; $R_F = 0.8$, toluene/ethyl acetate 8:2.

(f) D,L-erythro-2-amino-1,3-dihydroxy-4-trans-octadecene (D,L-$C_{18}$-sphingosine)

This compound is prepared by the process in Angew.Chem. 94, 215-216 (1982); Angew.Chem.Int.Ed.Engl. 21, 210-211 (1982); Angew.Chem.Suppl. 1982, 393-397.

(g) D,L-erythro-2-amino-3-hydroxy-4-trans-eicosadecenoic acid

The compound is prepared by the same process as indicated for compound (f).

1.1 ml (7.9 mmol) of dry diisopropylamine is added, under nitrogen, to a solution, cooled to −40° C., of 5.8 mmol of n-butyllithium in 30 ml of anhydrous tetrahydrofuran which is saturated with nitrogen. The mixture is stirred at this temperature for 30 min and then cooled to −80° C. 1.6 g (5.6 mmol) of N,N-bis(trimethylsilyl)glycine trimethylsilyl ester (Angew.Chem. Int.Ed.Engl. 80, 797 (1968)) dissolved in a little tetrahydrofuran is slowly added dropwise, during which the solution turns yellow to brown. After 90 min., 2.2 g (8.4 mmol) of 2-trans-octadecenal, dissolved in tetrahydrofuran, are added dropwise. Stirring is allowed to continue at −80° C. for 90 min. The mixture is then warmed to room temperature and acidified to pH 5 with saturated ethanolic hydrochloric acid. After filtration with suction, the diisopropylamine hydrochloride and glycine hydrochloride are washed out with water. Yield: 1.6 g (88%). Melting point: 150° C. (decomposition).

| Elementary analysis for $C_{20}H_{39}NO_3$ (341.49) | | | |
|---|---|---|---|
| calculated: | C 70.34 | H 11.49 | N 4.10 |
| found: | 70.56 | 11.62 | 4.06 |

$^1$H NMR (in DMSO): 5.75–5.62 (m, 1H, —C$\underline{H}$=CH—CHOH); 5.42–5.30 (dd, 1H, C=C$\underline{H}$—CHOH, $J_{trans}$=15.5 Hz, $J_{vic}$=6.4 Hz); 4.28–4.20 (dd, 1H, —C=CH—C$\underline{H}$OH, $J_1$=$J_2$=6.1 Hz); 3.50–3.20 (m, OH, NH$_3$, H$_2$O); 3.17–3.12 (d, 1H, —C$\underline{H}$—COOH, J=6.1 Hz); 2.03–1.91 (m, 2H, C$\underline{H}_2$—C=C); 1.40–1.10 (m, 26H, aliphat.); 0.90–0.80 (t, 3H, —CH$_3$).

(h)
D,L-erythro-2-amino-1,3-dihydroxy-4-trans-eicosene (D,L-C$_{20}$-sphingosine 5.2 g (15.2 mmol) of compound (g) are suspended in 500 ml of anhydrous tetrahydrofuran. 4.1 g (1.7 mmol) of lithium aluminum hydride are added in small portions. The mixture is heated to boiling under reflux for 36 hours. Excess LiAlH$_4$ is destroyed by cautious dropwise addition of water. A readily filtered precipitate can be obtained after dropwise addition of 30 ml of 2N sodium hydroxide solution. The mixture is filtered, the solid is washed with tetrahydrofuran and the filtrate is evaporated to dryness. The residue is a pale yellowish waxy substance. Yield: 3.8 g (76%). Melting point: 58°–60° C.; $R_F$=0.2, chloroform/methanol 1:1.

$^1$H-NMR (in CDCl$_3$): 5.82–5.71 (m, 1H, —C$\underline{H}$=CH—CHOH); 5.51–5.43 (dd, 1H, —CH=C$\underline{H}$—CHOH, $J_{trans}$=15.5 Hz $J_{vic}$=7.3 Hz); 4.09–4.02 (dd, 1H, C=CH—C$\underline{H}$OH, $J_1$=$J_2$=6.1 Hz); 3.75–3.59 (m, 2H, —C$\underline{H}_2$OH); 2.94–2.85 (m, 1H, —C$\underline{H}$—NH$_2$); 2.49–2.15 (m, 3H, —NH$_2$, HO—CH—); 2.14–1.97 (m, 3H, —CH$_2$—OH, C=CH—C$\underline{H}_2$); 1.45–1.12 (m, 26H, aliphat.) 0.95–0.82 (t, 3H, —CH$_3$).

GENERAL PROCEDURE FOR THE SYNTHESIS OF THE CERAMIDES 2 g (6.1 mmol) of sphingosine are dissolved in 100 ml of tetrahydrofuran. 50 ml of 50% aqueous sodium acetate solution and 7.3 mmol of the particular fatty acid chloride, dissolved in 20 ml of anhydrous ether, are simultaneously added dropwise. The mixture is stirred at room temperature for 2 hours. The ether phase is separated off and extracted by shaking twice with 50 ml of aqueous sodium bicarbonate solution each time and with 50 ml of water. The organic phase is evaporated to dryness. The residue is recrystallized from 100 ml of methanol and once from 100 ml of n-hexane.

(i)
D,L-erythro-1,3-dihydroxy-2-palmitoylamino-4-transoctadecene 8 g (30 mmol) of sphingosine are dissolved in 200 ml of tetrahydrofuran and, with vigorous stirring, 100 ml of 50% sodium acetate solution was added. 11 g (40 mmol) of palmitoyl chloride, dissolved in 15 ml of anhydrous ether, are slowly added dropwise to this. The mixture is then stirred at room temperature for 1 hour. The aqueous phase is separated off and the organic phase is washed several times with saturated sodium bicarbonate solution. After drying over sodium sulfate and evaporation, the product is recrystallized from methanol. Yield: 10 g (70%), melting point 94°–96° C.

$R_F$=0.57, chloroform/methanol 9:1 (D,L-sphingosine: $R_F$=0.04), $^1$H NMR (80 MHz, CDCl$_3$ in ppm): 7.0 (brd, 1H, NH); 5.75 (m, 2H, HC=CH), 4.3 (m, 1H, —C$\underline{H}$—N); 4.1–3.6 (m, 5H).

(j)
D,L-erythro-1,3-dihydroxy-2-palmitoylamino-4-transeicosene

The synthesis is carried out by the general procedure. Yield: 2.66 g (77%). Melting point: 88°–89° C.; $R_F$=0.15, dichloromethane/methanol 95:5.

| Elementary analysis for $C_{36}H_{71}NO_3$ (565.89) | | | |
|---|---|---|---|
| calculated: | C 76.41 | H 12.63 | N 2.47 |
| found: | 76.22 | 12.61 | 2.47 |

1H NMR (in CDCl$_3$): 6.29–6.19 (d, 1H, N$\underline{H}$, J=8.8 Hz); 5.88–5.71 (m, 1H, C$\underline{H}$—CH—CHOH); 5.60–5.47 (dd, 1H, HC=C$\underline{H}$—CHOH, $J_{trans}$=15.5 Hz, $J_{vic}$=6.7 Hz); 4.39–4.29 (m, 1H, C$\underline{H}$—NH); 4.02–3.88 (m, 2H, C=C—C$\underline{H}$OH, C$\underline{H}_2$OH); 3.78–3.67 (m, 1H, C$\underline{H}_2$OH); 2.68–2.55 (m, 1H, O$\underline{H}$); 2.29–2.19 (t, 2H, CO—C$\underline{H}_2$, J=7.6 Hz); 2.12–2.01 (m, 2H, C=C—C$\underline{H}_2$); 1.70–1.61 (m, 2H, CO—CH$_2$—C$\underline{H}_2$); 1.45–1.15 (m, 50H, aliphat.); 0.95–0.83 (t, 6H, CH$_3$).

(k)
D,L-erythro-1,3-dihydroxy-2-stearoylamino-4-transeicosene

The synthesis is carried out by the general procedure. Yield: 2.42 g (67%), melting point: 90°–91° C.; $R_F$=0.15, dichloromethane/methanol 95:5.

| Elementary analysis for $C_{38}H_{75}NO_3$ (595.95) | | | |
|---|---|---|---|
| calculated: | C 76.84 | H 12.71 | N 2.36 |
| found: | 76.64 | 12.73 | 2.33 |

$^1$H NMR (in CDCl$_3$): 6.28–6.19 (d, 1H, N$\underline{H}$, J=8.8 Hz); (m, 1H, CHCH—CHOH); 5.60–5.47 (dd, 1H, C=C$\underline{H}$—CHOH, $J_{trans}$=15.5 Hz, $J_{vic}$=6.7 Hz); 4.37–4.28 (m, 1H, C$\underline{H}$—NH); 4.00–3.87 (m, 2H, C=C—C$\underline{H}$OH, C$\underline{H}_2$OH); 3.77–3.67 (m, 1H, C$\underline{H}_2$OH), 2.95–2.85 (m, 2H, O$\underline{H}$); 2.28–2.18 (t, 2H, CO—C$\underline{H}_2$); 2.11–2.00 (m, 2H, C=C—C$\underline{H}_2$, J=7.6 Hz); 1.75–1.58 (m, 2H, CO—C$\underline{H}_2$); 1.45–1.11 (m, 54H, aliphat); 0.95–0.83 (t, 6H, —CH$_3$).

(l)
D,L-erythro-1,3-dihydroxy-2-tetracosanoylamino-4-trans-eicosene

The synthesis is carried out by the general procedure. However, 100 ml of anhydrous ether are necessary to dissolve the tetracosanoyl chloride. Yield: 2.64 g (64%), melting point 93°–94° C.; $R_F$=0.15, dichloromethane/methanol 95:5.

| Elementary analysis for $C_{44}H_{87}NO_3$ (687.09): | | | |
|---|---|---|---|
| calculated: | C 77.93 | H 12.92 | N 2.06 |
| found: | 77.98 | 13.02 | 2.21 |

$^1$H NMR (in CDCl$_3$): 6.30–6.25 (d, 1H, NH, J=8.8 Hz); (m, 1H, CH=C—CHOH); 5.59–5.47 (dd, 1H, CH=CH—CHOH, $J_{trans}$=15.5 Hz, $J_{vic}$=6.7 Hz); 4.36–4.27 (m, 1H, CH—NH); 4.00–3.87 (m, 2H, C=C—CHOH, CH$_2$OH); 3.75–3.65 (m, 1H, CH$_2$OH); 2.85–2.73 (m, 2H, OH), 2.27–2.17 (t, 2H, CH—CH$_2$, J=7.6 Hz); 2.10–2.00 (m, 2H, C=C—CH$_2$); 1.70–1.55 (m, 2H, CO—CH$_2$—CH$_2$); 1.44–1.15 (m, 66H, aliphat.); 0.93–0.82 (t, 6H, —CH$_3$).

EXAMPLE 1

D- and L-erythro-1-O-β-D-glucopyranosyloxy-3-hydroxy-2-palmitoylamino-4-trans-octadecene (1)
D,L-erythro-3-hydroxy-2-palmitoylamino-1-(triphenylmethyloxy)-4-trans-octadecene The compound is prepared in analogy to the process in Chem.Phys.Lipids 3, 59–69 (1969).

1.08 g (2 mmol) of compound (j) are dissolved in a mixture of 6 ml of anhydrous pyridine, 6 ml of anhydrous chloroform and 6 ml of anhydrous tetrahydrofuran and 0.56 g (4 mmol) of trityl chloride is added. After a reaction time of 48 hours at room temperature, the mixture is poured onto water and extracted with ether. After drying over sodium sulfate and evaporation, chromatography is carried out on silica gel with toluene/ethyl acetate 9:1.

For analysis, chromatography is carried out under medium pressure with toluene/ethyl acetate 9:1. Yield: 0.94 g (60%).

Melting point 58°–60° C.; $R_F$=0.64, toluene/acetone 8:2 (yellow-brown color with H$_2$SO$_4$) (compound (e): $R_F$=0.12).

$^1$H NMR (250 MHz, CDCl$_3$ in ppm): 7.3 (m, 15H, trityl); 6,07 (d, 1H, NH, J=7.6 Hz); 5.62 (td, 1H, —CH$_2$—CH=C, J=7.6 Hz); J=15.2 Hz);, 5.25 (dd, 1H, C=CH—CH, J=6.1 Hz, J=15.2 Hz); 4.18 (m, 1H, —CH—N); 4.05 (m, 1H, —CH—O); 3.34 (dd, 1H, —CH$_2$—O); 3.28 (dd, 1H, —CH$_2$—O, J=4.0 Hz, J=9.8 Hz); 2.2 (dd, 2H, CO—CH$_2$—, J=7.9 Hz).

(2) D- and L-erythro-3-(L(+)-O-acetylamandeloyloxy)-2-palmitoylamino-1-(triphenylmethyloxy)-4-trans-octadecene 220 mg (0.28 mmol) of the compound D-(1) or L-(1) obtained in accordance with the above section, and 240 mg (0.84 mmol) of L-(+)-acetylmandeloyl chloride are dissolved in 5 ml of anhydrous toluene and 1.2 ml of anhydrous pyridine. After 1 hour, precipitation of the pyridine hydrochloride is complete. The mixture is diluted with 10 ml of ether and washed with water, dried over sodium sulfate and evaporated. The two isomers are separated by medium pressure chromatography using toluene/ethyl acetate 95:5. Yield: 200 mg (75% overall; compound D-(2): 38%, compound L-(2): 37%.

Compound D-(2): $R_F$=0.44, Compound L-(2): $R_F$=0.51 (compound (l): $R_F$=0.25), toluene/ethyl acetate 9:1.

$^1$H NMR (250 MHz, CDCl$_3$ in ppm): compound D-(2): 7.35 (m, 15H, trityl); 5.85 (d, 1H, NH, J=9.8 Hz); 5.83 (s, 1H, —CH(Ph)OAc); 5.56 (m, 1H, -CH-O-mandeloyl); 5.46 (td, 1H, —CH$_2$—CH=C, J=7.6 Hz, J=15.2 Hz); 5.1 (dd, 1H, C=CH—CH, J=6.1 Hz, J=15.2 Hz); 4.3 (m, 1H, —CH—N); 3.35 (dd, 1H, —CH$_2$—O, J=9.4 Hz, J=5 Hz); 3.19 (dd, 1H, —CH$_2$—O, J=9.4 Hz, J=5 Hz).

Compound L-(2): 7.3 (m, 15H, trityl); 5.79 (s, 1H, —CH(Ph)OAc); 5.64 (td, 1H, —Ch$_2$—CH=C, J=15.2 Hz, J=7.6 Hz); 5.39 (m, 1 Hz, -CH-O-mandeloyl); 5.25 (dd, 1H, —C=CH—CH, J=15.2 Hz, J=6.9 Hz); 4.22 (m, 1H, —CH—N); 3.08 (dd, 1H, —CH$_2$O, J=9.4 Hz, J=5.0 Hz); 2.95 (dd, 1H, —CH$_2$—O, J=9.4 Hz, J=6.25 Hz).

(3) D- and L-erythro-3-hydroxy-2-palmitoylamino-1-(triphenylmethyloxy)-4-trans-octadecene 1 g (1.05 mmol) of compound D-(2) or L-(2) is dissolved in 50 ml of anhydrous methanol and 10 ml of anhydrous toluene, and 0.1 ml of 1M sodium methanolate solution is added, and the mixture is stirred at room temperature. After 12 hours, it is neutralized with ion exchanger, filtered and evaporated.

Yield: 0.8 g (95%).

Compound D-(3) or L-(3): $R_F$=0.64, toluene/acetone 8:2. The $^1$H NMR data of the two compounds are identical to those of the compound in Section (1).

(4) D- and L-erythro-3-benzoyloxy-2-palmitoylamino-1-(triphenylmethyloxy)-4-trans-octadecene 930 mg (1.2 mmol) of compound D-(3) or L-(3) and 0.6 ml (6 mmol) of benzoyl chloride are dissolved in 20 ml of anhydrous toluene and 3 ml of anhydrous pyridine, and the solution is stirred at room temperature for 1½ hours. It is diluted with 10 ml of ether, washed with saturated sodium bicarbonate solution, dried with sodium sulfate and evaporated. Silica gel chromatography using toluene/ethyl acetate 9:1 provides pure product. Yield: 1 g (95%).

$R_F$=0.48, toluene/ethyl acetate 9:1 $^1$H NMR (250 MHz, CDCl$_3$ in ppm): 7.93 (m, 2H, benzoyl); 7.55 (m, 1H, benzoyl); 7.4 (m, 8H, benzoyl, trityl); 5.88 (td, 1H, —CH$_2$—CH=C, J=15.2 Hz, J=6.7 Hz); 5.7 (m, 2H, NH, —CH—OBz); 5.44 (dd, 1H, C=CH—CH, J=15.2 Hz, J=7.6 Hz); 4.49 (m, 1H, CH—N); 3.45 (dd, 1H, —CH$_2$—O, J=9.2 Hz, J=3.4 Hz); 3.2 Hz (dd, 1H, —CH$_2$O—, J=9.2 Hz, J=4 Hz).

(5) D- and L-erythro-3-benzoyloxy-1-hydroxy-2-palmitoylamino-4-trans-octadecene 400 mg (0.45 mmol) of compound D-(4) or L-(4) are dissolved in 5 ml of anydrous toluene, and 0.18 ml of anhydrous methanol and 0.01 ml of boron trifluoride etherate are added. The starting material was no longer detectable after 10 minutes. The mixture is diluted with 5 ml of toluene, washed with water, dried over sodium sulfate and evaporated. For purification, the product is chromatographed on silica gel using toluene/acetone 9:1.

Yield: 200 mg (70%).

$R_F$=0.44, toluene/acetone 8:2. $^1$H NMR (250 MHz, CDCl$_3$ in ppm):8.04 (m, 2H, benzoyl); 7.6 (m, 1H, benzoyl); 7.47 (m, 2H, benzoyl); 6.05 (d, 1H, NH J=8.8 Hz); 5.86 (td, 1H, —CH$_2$—CH=C, J=14.7 Hz, J=6.7 Hz); 5.61 (dd, 1H, —C=CH—CH, J=14.7 Hz, J=7.6 Hz); 5.53 (m, 1H, —CH—OBz); 4.29 (m, 1H, —CH—N); 3.72 (m, 2H, —CH$_2$—O); 2.9 (m, 1H, —OH).

(6) D- and L-erythro-3-benzoyloxy-2-palmitoylamino-1-(2,3,4,6-tetra-O-acetyl-β-D-glucopyranosyloxy)-4-trans-octadecene 100 mg (0.16 mmol) of compound D-(5) or L-(5) and 180 mg (0.32 mmol) of O-(2,3,4,6-tetra-O-acetyl -α-D-glucopyranosyl) trichloroacetimidate are dissolved in 10 ml of anhydrous methylene chloride, and a spatula tip of powdered 0.4 nm molecular sieves (4 Å) and d2 ml of 0.1M boron trifluoride etherate in methylene chloride are added. After 3 hours, the mixture is diluted with 10 ml of chloroform, filtered to remove molecular sieves, washed with saturated sodium bicarbonate solution, dried over sodium sulfate and evaporated. For purification, the product is filtered through silica gel with toluene/acetone 9:1 and chromatograped under medium pressure using toluent/acetone 9:1. Yield: 78 mg (50%). $R_F$=0.55, toluene/acetone 8:2.

$^1$H NMR (250 MHz, CDCl$_3$ in ppm): Compound D-(6): 8.0 (m, 2H, benzoyl); 7.57 (m, 1H, benzoyl); 7.44 (m, 2H, benzoyl); 5.81 (m, 2H, NH, CH$_2$—CH=C); 5.42 (m, 2H, C=CH—CH—OBz); 5.15 (dd, 1H, H-4, J=7.5 Hz, J=7.5 Hz); 5.01 (m, 2H, H-3, H-2); 4.47 (m, 1H, NH); 3.39 (d, 1H, H-1, J=7.9 hz), 4.23 (dd, 1H, H-6, J=12.2 Hz, J=4.9 Hz); 4.04 (dd, 1H, H-6', J=12.2 Hz, J=2.1 Hz); 3.9 (dd, 1H, —CH$_2$—O—, J=9.8 Hz, J=3.05 Hz); 3.68 (m, 2H, —CH$_2$—O, H-5); 2.1 (s, 3H, acetyl); 2.04 (s, 3H, acetyl); 1.99 (s, 6H, acetyl).

Compound L-(6): 8.04 (m, 2H, benzoyl); 7.58 (m, 1H, benzoyl); 7.45 (m, 2H, benzoyl); 5.95-5.72 (m, 2H, NH, —CH$_2$—CH=C); 5.6-5.3 (m, 2, —C=CH—OBz); 5.25-4.95 (m, 3H, H-4, H-3, H-2); 4.45 (m, 2H, -H-1-CH-N); 4.3-3.85 (m, 3H); 3.65 (m, 2H).

(7) D- and L-erythro-1-(β-D-glucopyranosyloxy)-3-hydroxy-2-palmitoylamino-4-trans-octadecene 100 mg (0.1 mmol) of compound D-(6) or L-(6) are suspended in 5 ml of anhydrous methanol, and a catalytic amount of sodium metal is added. After 15 min, neutralization is carried out with ion exchanger in the acid form, during which the solution becomes cloudy. It is heated and filtered. After evaporation, the residue is purified by chromatography on a short silica gel column using chloroform/methanol 9:1. Yield: 70 mg (100%). $R_F$=0.4, chloroform/methanol 85:15.

$^1$H NMR (250 MHz, DMSO in ppm): Compound D-(7): 7.5 (d, 1H, NH, J=8.7 Hz); 5.52 (m, 1H, —CH$_2$—CH=C); 5.35 (dd, 1H, C=CH—, J=15.2 Hz, J=6.5 Hz); 5.03 (d, 1H, OH, J=4.3 Hz); 4.92 (m, 3H, OH); 4.5 (t, 1H, OH, J=4.9 Hz); 4.09 (d, 1H, H-1, J=8.2 Hz); 4.0-3.55 (m, 4H), 3.45 (m, 2H); 3.15-2.9 (m, 4H); 2.1-1.9 (m, 4H); 1.45 (m, 2H); 1.22 (brs, 46H, —CH$_2$—); 0.85 (m, 6H, CH$_3$).

Compound L-(7): 7.47 (d. 1H. NH, J=9.1 Hz); 5.52 (td, 1H, CH$_2$—CH=C, J=15.2 Hz, J=6.1 Hz); 5.34 (dd, 1H, C=CH—CH, J=15.2 Hz, J=6.7 Hz); 4.9 (m, 3H, OH); 4.59 (m, 1H, OH); 4.13 (d, 1H, H-1, J=7.3 Hz); 4.0-2.91 (m, 10H); 2.12-1.85 (m, 4H, CO—CH$_2$, C=C—CH$_2$); 1.58-1.09 (m, 48H, CH$_2$ aliphat.); 0.85 (m, 6H, CH$_3$).

EXAMPLE 2

(8)

D,L-erythro-3-hydroxy-1-(diphenyl-p-methoxyphenylmethyloxy)-2-stearoylamino-4-trans-eicosene 2 g (3.3 mmol) of compound (k) and 1.56 g (5 mmol) of monomethoxytrityl chloride in 30 ml of a mixture of tetrahydrofuran, chloroform, and pyridine 1:1:1, anhydrous in each case, are stirred in room temperature for 2 hours. The mixture is poured onto 100 ml of water and extracted twice with 50 ml of ether. The organic phase is dried over sodium sulfate and evaporated to dryness. Chromatography is carried out on silica gel using toluene/ethyl acetate 8.5:1.5. Yield: 2.1 g (73%). Melting point 49°-51° C. $R_F$=0.27, toluene/ethyl acetate 8.5:1.5.

| Elementary analysis for C$_{58}$H$_{91}$NO$_4$ (866.28) | | | |
|---|---|---|---|
| calculated: | C 80.42 | H 10.58 | N 1.62 |
| found: | 80.23 | 10.79 | 1.74 |

$^1$H-NMR (in CDCl$_3$): 7.42-7.20 (m, 12 H, aromat.); 6.87-6.80 (m, 2H, aromat.); 6.10-6.04 (d, 1H, NH, J=7.9 Hz); 5.73-5.57 (m, 1H, CH=CH—CHOH); 5.32-5.20 (dd, 1H, CH=CH—CHOH, J$_{vic}$=6.4 Hz, J$_{trans}$=15.5 Hz); 4.22-4.14 (m, 1H, CH—NH); 4.10-4.02 (m, 1H, CH—OH); 3.79 (s, 3H, OCH$_3$); 3.45-3.28 (m, 3H, OH, CH$_2$OH); 2.25-2.17 (t, 2H, C=C—CH$_2$, J=7.6 Hz); 1.97-1.88 (m, 2H, CH$_2$—C=C); 1.70-1.60 (m, 2H, C=C—CH$_2$—CH$_2$); 1.40-1.15 (m, 54H, aliphat.); 0.95-0.82 (t, 6H, —CH$_3$).

(9) D- and L-erythro-3-(L(+)-O-acetylmandeloyloxy)-1-(diphenyl-p-methoxyphenylmethyloxy)-2-stearoylamino-4-trans-eicosene 4.3 g (5 mmol) of compound D,L-(8) are dissolved in 50 ml of a mixture of anhydrous toluene and anhydrous pyridine 4:1. 3.2 g (15 mmol) of L(+)-O-acetylmandeloyl chloride are added. The mixture is stirred at room temperature for 2 hours. After dilution with 100 ml of ether, the mixture is extracted by shaking twice with 50 ml of water. The organic phase is dried over sodium sulfate and evaporated. After chromatography on silica gel using toluene/ethyl acetate 95:5, the diastereomers D-(9) and L-(9) can be separated by medium pressure chromatography on silica gel using toluene/ethyl acetate 96:4.

Compound D-(9): yield: 1.8 g (35%, relative to the total amount of compound (k). Melting point 59°-61° C., $R_F$=0.44, toluene/ethyl acetate 95:5.

$^1$H NMR (in CDCl$_3$): 7.50-7.17 (m, 17H, aromat.); 6.86-6.80 (m, 2H, aromat.); 5.85-5.80 (m, 2H, NH; CO—CH—OAc); 5.60-5.52 (m, 1H, CH—OAc.mand.); 5.45-5.30 (m, 1H, CH=CH—CHO—); 5.17-5.05 (dd, 1H, CH=CH—CHO—, J$_{trans}$=15.5 Hz, J$_{vic}$=6.1 Hz); 4.35-4.24 (m, 1H, CH—NH—); 3.8 (s, 3H, OCH$_3$); 3.39-3.30 (dd, 1H, CH$_2$O—, J$_{gem}$=9.7 Hz, J$_{vic}$=3.9 Hz); 3.22-3.14 (dd, 1H, CHO—, J$_{gem}$=9.7 Hz, J$_{vic}$=4.2 Hz);

2.22 (s, 3H, OAc); 2.12-2.03 (t, 2H, CO—CH$_2$, J=7.6 Hz); 1.85-1.75 (m, 2H, C=C—CH$_2$); 1.60-1.50 (m, 2H, CO—CH$_2$—CH$_2$); 1.40-1.07 (m, 54H, aliphat.); 0.94-0.82 (t, 6H, CH$_3$).

Compound L-(9): yield: 1.6 g (31%, relative to the total amount of compound (k). Melting point 34°-35° C. R$_F$=0.52, toluene/ethyl acetate 95:5.

$^1$H NMR (in CDCl$_3$): 7.50-7.17 (m, 17H, aromat.); 6.86-6.80 (m, 2H, aromat.); 5.88 (s, 1H, CO—CH—OAc); 5.79-5.65 (m, 1H, CH=CH—CHO—); 5.50-5.24 (m, 2H, CH=CH—CHO—, CH—OAc.-mand.); 5.17-5.09 (d, 1H, NH, J=9.2 Hz); 4.35-4.24 (m, 1H, CHNH); 3.80 (s, 3H, OCH$_3$); 3.18-3.10 (dd, 1H, CH$_2$—O—, J$_{gem}$=9.7 Hz, J$_{vic}$=3.9 Hz); 3.06-2.98 (dd, 1H, CH$_2$—O—, J$_{gem}$=9.7 Hz, J$_{vic}$=4.2 Hz); 2.10 (s, 3H, OAc); 1.89-1.80 (t, 2H, CO—CH$_2$); 1.65-1.40 (m, 4H, C=C—CH$_2$, CO—CH$_2$); 1.38-1.10 (m, 54H, aliphat.); 0.94-0.82 (t, 6H, CH$_3$).

The compounds D-(9) and L-(9) were converted into the corresponding enantiomeric ceramides by elimination of the monomethoxytrityl and acetylmandeloyl radicals. The ceramides thus obtained were identical to compound (k) by $^1$H NMR spectroscopy.

(10)
D-erythro-3-(L(+)-O-acetylmandeloyloxy)-1-hydroxy-2-stearoylamino-4-trans-eicosene 1 g (0.95 mmol) of compound D-(9) is dissolved in 50 ml of a mixture of dichloromethane and methanol 4:1 which contains 1% p-toluenesulfonic acid. The mixture is stirred at room temperature for 1 hour. It is then extracted by shaking twice with aqueous sodium bicarbonate solution. After evaporation, the product is chromatographed on silica gel toluene/ethyl acetate 7.5:2.5. Yield: 0.47 g (65%). Melting point 76°-77° C.; R$_F$=0.46, dichloromethane/methanol 95:5.

$^1$H NMR (in CDCl$_3$): 7.50-7.36 (m, 5H, aromat.); 6.06-6.00 (d, 1H, NH, J=8.2 Hz); 5.78 (s, 1H, CO—CH—OAc); 5.57-5.28 (m, 2H, CH=CH); 4.25-4.13 (m, 1H, CH—NH); 3.87-3.75 (m, 1H, CH$_2$OH); 3.72-3.60 (m, 1H, CH$_2$OH); 2.52-2.40 (m, 1H, OH); 2.23 (s, 3H, OAc) 2.22-2.13 (t, 2H, CO—CH$_2$, J=7.6 Hz); 1.95-1.83 (m, 2H, C=C—CH$_2$); 1.65-1.52 (m, 2H, CO—CH$_2$—CH$_2$); 1.37-1.10 (m, 54H, aliphat.); 0.95-0.82 (t, 6H, CH$_3$).

EXAMPLE 3

(12)
D,L-erythro-3-hydroxy-2-stearoylamino-1-(triphenylmethyloxy)-4-trans-eicosene 2.4 g (4 mmol) of compound (k) and 2.5 g (8.9 mmol) of trityl chloride in 45 ml of a mixture of tetrahydrofuran, chloroform and pyridine 1:1:1, anhydrous in each case, are stirred at room temperature for 48 hours. The solution is poured onto 200 ml of water and extracted twice with 100 ml of ether. The ether phase is washed twice with 50 ml of 0.1N hydrochloric acid and then extracted by shaking with 100 ml of aqueous sodium bicarbonate solution. The organic phase is dried over sodium sulfate and evaporated to dryness. The residue is then chromatographed on silica gel using toluene/ethyl acetate 9:1. Yield: 2 g (60%); melting point 69°-70° C.; R$_F$=0.55, toluene/acetone 8:2.

| Elementary analysis for C$_{57}$H$_{89}$NO$_3$ (836.26) | | | |
|---|---|---|---|
| calculated: | C 81.86 | H 10.71 | N 1.67 |

| Elementary analysis for C$_{57}$H$_{89}$NO$_3$ (836.26) -continued | | | |
|---|---|---|---|
| found: | 81.74 | 10.72 | 1.74 |

$^1$H NMR (in CDCl$_3$): 7.44-7.20 (m, 15H, aromat.); 6.11-6.05 (d, 1H, NH, J=7.6 Hz); 5.71-5.57 (m, 1H, CH=CH—CHOH); 5.32-5.20 (dd, 1H, CH=CH—CHOH, J$_{trans}$=15.5 Hz, J$_{vic}$=5.7 Hz); 4.23-4.14 (m, 1H, CH—NH); 4.12-4.02 (m, 1H, —CHOH); 3.45-3.36 (m, 2H, OH, CH$_2$OH); 3.34-3.27 (dd, 1H, CH$_2$OH, J$_{gem}$=9.5 Hz, J$_{vic}$=3.6 Hz); 2.27-2.18 (t, 2H, CO—CH$_2$, J=7.6 Hz); 1.98-1.88 (m, 2H, C=C—CH$_2$); 1.71-1.60 (m, 2H, CH—CH$_2$—CH$_2$); 1.40-1.14 (m, 54H, aliphat.); 0.95-0.83 (t, 6H, —CH$_3$).

EXAMPLE 4

D- and L-erythro-3-hydroxy-1-(β-D-glucopyranosyloxy)-2-palmitoylamino-4-trans-octadecene

(13) D- and L-erythro-3-(L(+)-0-acetylmandeloyloxy)-1-hydroxy-2-palmitoylamino-4-trans-octadecene 400 mg (0.42mmol) of compound D-(2) or L-(2) from Example 1(2) are dissolved in 4 ml of anhydrous toluene, and 0.2 ml of anhydrous methanol is added. With exclusion of moisture and vigorous stirring, 0.1 ml (0.84 mmol) of boron trifluoride etherate is added, the solution briefly turning yellow. The starting material was no longer present (TLC) after 15 min. The mixture was diluted with toluene, washed with water, dried over sodium sulfate and the solvent is removed in vacuo.

For purification, the product is chromatographed on silica gel using toluene/acetone 9:1. Yield: 180 mg (60%).

Compound D-(13): R$_F$=0.4, toluene/acetone 8:2; compound L-(13): R$_F$=0.44, toluene/acetone 8:2.

$^1$H NMR (250 MHz, CDCl$_3$ in ppm): Compound D-(13): 7.41 (m, 5H, phenyl); 6.2 (d, 1H, NH, J=8.2 Hz); 5.8 (s, 1H, —CH—OAc); 5.6-5.25 (m, 3H, CH=CH, —CH—O-mandeloyl); 4.2 (m, 1H, CH—N); 3.81 (dd, 1H, —CH$_2$—OH, J=12.7 Hz, J=4.8 Hz); 3.65 (dd, 1H, —CH$_2$—OH, J=12.7 Hz); 2.45 (m, 1H, OH); 2.2 (s, 3H, —CO—CH$_3$); 2.18 (m, 2H, aliphat.); 1.9 (m, 2H, aliphat.); 1.55 (m, 4H, aliphat.); 1.22 (m, 44H, aliphat.); 0.88 (m, 6H, —CH$_3$).

Compound L-(13): 7.4 (m, 5H, phenyl); 5.86 (s, 1H, —CH—OAc); 5.8-5.62 (m, 2H, —CH=CH—CH—O, NH); 5.48-5.3 (m, 2H, —CH=CH—CH—O-mandeloyl); 4.0 (m, 2H, —CH—N, OH); 3.5 (dd, 1H, —CH$_2$—O, J=4.6 Hz); 3.35 (dd, 1H, —CH$_2$—O, J=11.6 Hz, J=5.2 Hz); 2,2 (s, 3H, —CO—CH$_3$); 1.96 (m, 4H aliphat.); 1.5 (m, 2H, aliphat.); 1.2 (m, 46H, aliphat.); 0.85 (m, 6H, —CH$_3$).

| Elementary analysis for C$_{44}$H$_{75}$NO$_6$ (714.09) | | | |
|---|---|---|---|
| calculated: | C 74.01 | H 10.59 | N 1.96 |
| found: | 73.48 | 10.64 | 2.06 |

(14) D- and L-erythro-1-(2,3,4,6-tetra-0-acetyl-β-D-glucopyranosyloxy)-3-(L(+)-0-acetylmandeloyloxy)-2-palmitoylamino-4-trans-octadecene 350 mg (0.49 mmol) of compound D-(13) or L-(13) and 400 mg (0.8 mmol) of 0-(2,3,4,6-tetra-0acetyl-α-D- glycopyranosyl) trichloroacetimidate are dissolved in 30 ml of anhydrous methylene chloride, and a spatula tip of powdered molecular sieves 0.4 nm (4 Å) is added. With exclusion of moisture and thorough stirring, 1 ml of boron trifluoride etherate is added. After 2 hours, starting material is no longer present (TLC). The mixture is washed with saturated sodium bicarbonate solution, dried over sodium sulfate and the solvent is removed in vacuo. For purification, the product is chromatographed on silica gel using toluene/acetone 9:1 and then under medium pressure using toluene/acetone 9:1. Yield: 300 mg (59%).

Compound D-(14): $R_F=0.58$, toluene/acetone 8:2; compound L-(14): $R_F=0.6$, toluene/acetone 8:2.

| Elementary analysis for $C_{58}H_{93}NO_{15}$ (1,044.37) | | | |
| --- | --- | --- | --- |
| calculated: | C 66.70 | H 8.98 | N 1.34 |
| found: | 66.16 | 9.11 | 1.24 |

(15) D- and L-erythro-3-hydroxy-1-(β-D-glucopyranosyloxy)-2-palmitoylamino-4-trans-octadecene 120 mg (0.11 mmol) of compound D-(14) or L-(14) are dissolved in 6 ml of anhydrous methanol, and 0.05 ml of a 1M sodium methanolate solution is added and the mixture is stirred at room temperature. After 2 hours, it is neutralized with ion exchanger in the acid form, slight cloudiness occurring. The mixture is heated, filtered to remove the ion exchanger which is washed with methanol, and evaporated to dryness. For purification, the product is chromatographed on silica gel using chloroform/methanol 85:15. Yield: 75 mg (97%).

compound D-(15): $R_F=0.6$, chloroform/methanol 8:2;
compound L-(15): $R_F=0.6$, chloroform/methanol 8:2.

The compounds are identical to compounds D-(7) and L-(7) respectively obtained in Example 1.

EXAMPLE 5

D- and L-erythro-1-O-β-D-glucopyranosyloxy-3-hydroxy-2-palmitoylamino-4-trans-octadecene

(16)
D,L-erythro-3-benzoyloxy-2-palmitoylamino-1-(triphenylmethyloxy)-4-trans-octadecene 250 mg (0.32 mmol) of D,L-erythro-3-hydroxy-2-palmitoylamino-1-(triphenylmethyloxy)-4-trans-octadecene (compound (1)) are dissolved in 6 ml of anhydrous toluene and 1 ml of anhydrous pyridine. 0.25 ml (1.5 mmol) of benzoyl chloride are added, and the mixture is stirred at room temperature for 1½ hours. It is diluted with 10 ml of ether, washed with saturated sodium bicarbonate solution, dried over sodium sulfate and evaporated to dryness. For purification, the product is chromatographed on silica gel using toluene/ethyl acetate 9:1. The product is identical by $^1H$ NMR spectroscopy to compound D-(4) or L-(4) prepared in Example 1. Yield: 260 mg (92%). $R_F=0.48$, toluene/ethyl acetate 9.1.

(17)
D,L-erythro-3-benzoyloxy-1-hydroxy-2-palmitolamino-4-trans-octadecene 700 mg (0.79 mmol) of D,L-erythro-3,0-benzoyl-2-palmitoamino-1-(triphenylmethyloxy)-4-trans octadecene (compound (16)) are dissolved in 10 ml of anhydrous toluene, and 0.25 ml of anhydrous methanol and 0.14 ml of boron trifluoride etherate are added. After 10 min, the starting material was no longer present (TLC). The mixture is diluted with 10 ml of toluene, washed with water, dried over sodium sulfate and evaporated to dryness. For purification, the product is chromatographed on silica gel using toluene/acetone 9:1. The product is identical by $^1H$ NMR spectroscopy to compound D-(5) or L-(5) prepared in Example 1. Yield: 350 mg (69%). $R_F=0.44$, toluene/acetone 8.2.

(18) D- and L-erythro-3-benzoyloxy-2-palmitoylamino-1-(2,3,4,6-tetra-O-acetyl-β-D-glucopyranosyloxy)-4-trans-octadecene 200 mg (0.31 mmol) of D,L-erythro-3-benzoyloxy-1-hydroxy-2-palmitoylamino-4-trans-octadecene (compound (17)) and 200 mg (0.4 mmol) of 0-(2,3,4,6-tetra-0-acetyl-β-D-glucopyranosyl) trichloroacetimidate are dissolved in 10 ml of anhydrous methylene chloride, and a spatula tip of powdered molecular sieves 0.4 nm (4 Å) is added. After addition of 0.4 ml of 0.1M trimethylsilyl trifluoroacetate solution in methylene chloride, the mixture is stirred at room temperature for 6 hours. It is diluted with chloroform, filtered to remove molecular sieves, washed with saturated sodium bicarbonate solution, dried over sodium sulfate and evaporated to dryness. The product is chromatographed on silica gel using toluene/acetone 9:1 and, to separate the diasteromers, under medium pressure using toluene/acetone 9:1 on silica gel. The resulting products are identical to compounds D-(6) and L-(6) prepared in Example 1. Yield: 160 mg (50%, 25% D- and 25% L-compounds).

compound D-(18): $R_F=0.55$, toluene/acetone 8:2;
compound L-(18): $R_F=0.54$, toluene/acetone 8:2.

The acetyl groups are eliminated by the method described in Example 1(7); the products obtained prove to be identical to compounds D-(7) and L-(7) prepared in Example 1.

EXAMPLE 6

D- and L-erthro-1-O-β-D-glucopyranosyloxy-3-hydroxy-2-tetracosanoyloamino-4-trans-eicosene

(19)
D,L-erythro-3-hydroxyl-1-(diphenyl-p-methoxyphenylmethyloxy)-2-tetracosanoylamino-4-trans-eicosene 6 g (7.2 mmol) of compound (l) and 3.43 g (11 mmol) of monomethoxytrityl chloride in 50 ml of anhydrous pyridine are stirred at room temperature for 5 hours. The mixture is poured on 200 ml of water and extracted twice with 100 ml of ether. The organic phase is dried over sodium sulfate and evaporated to dryness. Chromatography is carried out on silica gel using toluene/ethyl acetate 8.5:1.5. Yield: 4.13 g (65%). $R_F=0.27$, toluene/ethyl acetate 85:15.

(20)
D,L-erythro-3-benzoyloxy-1-(diphenyl-p-methyoxy-phenylmethyloxy)-2-tetracosanoylamino-4-trans-eicosene 4 g (4.2 mmol) of compound (19) and 5 g (34 mmol) of benzoyl chloride in 30 ml of anhydrous pyridine are stirred at room temperature for 12 hours. The mixture is poured on 200 ml of water and extracted twice with 100 ml of ether. The organic phase is dried over sodium sulfate and evaporated to dryness. Chromatography is carried out an silica gel using toluene/ethyl acetate 9:1. Yield: 3 g (66%). $R_F=0.64$, toluene/ethyl acetate 85:15.

D,L-erythro-3-benzoyloxy-1-hydroxy-2-tetracosanoyloamino-4-trans-eicosene 3 g (2.8 mmol) of compound (20) are dissolved in a mixture of dichloromethane and methanol 4.1 which contains 1% by weight of p-toluenesulfonic acid, and the mixture is stirred at room temperature for one hour. It is then extracted by shaking with 30 ml of saturated, aqueous sodium bicarbonate solution. The organic phase is dried over sodium sulfate and the solvent is removed in vacuo. The product is chromatographed on silica gel using dichloromethane/methanol 97:3. Yield: 1,5 g (67%). $R_F=0.58$ dichloromethane/methanol 95.5.

(22) D- and
L-erythro-3-benzoyloxy-2-tetracosanoylamino-1-(2,3,4,6-tetra-O-acetyl-$\beta$-D-glucopyranosyloxy)-4-trans-eicosene 150 mg (0.19 mmol) of compound (21) and 180 mg (0.32 mmol) of O-(2,3,4,6-tetra-O-acetyl-$\alpha$-D-glucopyranosyl) trichloroacetimidate are dissolved in 10 ml of anhydrous methylene chloride, and a spatula tip of powered molecular sieves of 0.4 nm (4 Å) and 2 ml of 0.1M boron trifluoride etherate in methylene chloride are added. After 3 hours, the mixture is diluted with 10 ml of chloroform, the molecular sieves are removed by filtration, the filtrate is washed with a saturated sodium bicarbonate solution, dried over sodium sulfate and concentrated. For purification, the product is filtrated on silica gel using toluene/acetone 9:1.

The diastereomers D-(22) and L-(22) are separated by chromatography under medium pressure using toluene/acetone 9.1.

Yield:
D-(22) 40 mg (18%); $R_F=0.55$ toluene/acetone 8:2.
L-(22) 40 mg (18%); $R_F=0.52$ toluene/acetone 8:2.
$^1$H-NMR (250 MHz, CDCl$_3$ in ppm):
Compound D-(22): 8.0 (m, 2H, benzoyl);
7.57 (m, 1H, benzoyl); 7.44 (m, 2H, benzoyl);
5.81 (m, 2H, NH, CH$_2$—CH=C); 5.42 (m, 2H, C=CH—CH—Obz); 5.15 (dd, 1H, H-4, J=7.5 Hz, J=7.5 Hz); 5.01 (m, 2H, H-3, H-2); 4.47 (m, 1H, NH); 3.39 (d, 1H, H-1, J=7.9 Hz); 4.23 (dd, 1H, H-6, J=12.2 Hz, J=4.9 Hz); 4.04 (dd, 1H, H-6', J=12.2 Hz, J=2.1 Hz); 3.9 (dd, 1H, —CH$_2$—O—, J=9.8 Hz, J=3.05 Hz); 3.68 (m, 2H, —CH$_2$—O, H-5);
2.1 (s, 3H, acetyl); 2.04 (s, 3H, acetyl); 1.99 (s, 6H, acetyl).
Compound L-(22): 8.04 (m, 2H, benzoyl); 7.58 (m, 1H, benzoyl); 7.45 (m, 2H, benzoyl); 5.95–5.72 (m, 2H, NH, —CH$_2$—CH=C); 5.6–5.3 (m, 2H, —CH=CH—Obz); 5.25–4.95 (m, 3H, H-4, H-3, H-2); 4.45 (m, 2H, H-1 CH—N); 4.3–3.85 (m, 3H); 3.65 (m, 2H).

(23) D- and
L-erythro-1-O-$\beta$-D-glucopyranosyloxy-3-hydroxy-2-tetracosanoylamino-4-trans-eicosene 55.6 mg (0.05 mmol) of compound D-(22) or L-(22) are dissolved in 3 ml of anhydrous methanol, 0.03 ml of a 1M sodium methanolate solution is added and the mixture is stirred at room temperature. After one hour, it is neutralized with a ion exchanger in the acid form, slight cloudiness occurring. The mixture is heated, filtered to remove the ion exchanger which is washed with methanol, and evaporated to dryness. For purification, the product is chromatographed on silica gel using chloroform/methanol 85:15. Yield: 42 mg (95%). Compound D-(23): $R_F=0.7$, chloroform/methanol 8:2; compound L-(23): $R_F=017$, chloroform/methanol 8:2.

We claim:
1. A process for preparing sphingosine derivatives selected from the formula (I)-D and (I)-L

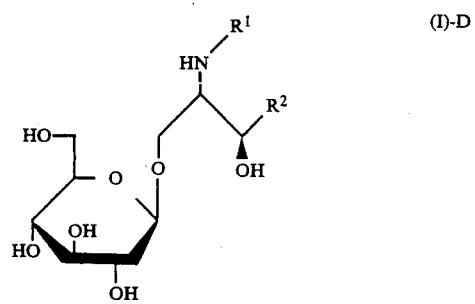

(I)-D

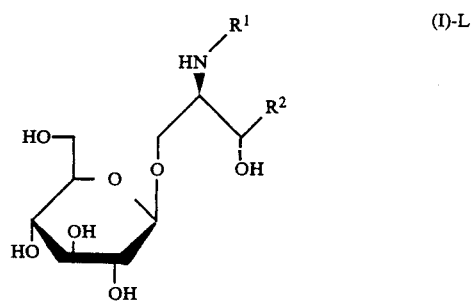

(I)-L in which R$^1$ denotes an acyl radical selected from the group consisting of radicals of fatty acids having 14 to 24 carbon atoms and the corresponding acyl radicals having a hydroxyl group in the $\alpha$-position of having 1 or 2 double bonds in the cis configuration, and R$^2$ denotes a radical selected from the group consisting of the pentadecanyl and the heptadecanyl radical and the corresponding C$_{15}$ and C$_{17}$ radicals having 1, 2 or 3 double bonds, one of which in each case being located in the 1, 2-position and having the trans configuration, the other, or others, when present, having the cis configuration; comprising reacting an optical active compound of the formula (II)-D or (II)-L

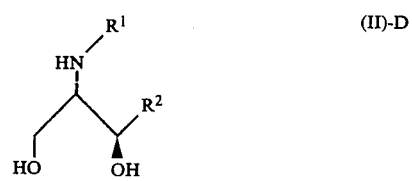

(II)-D

-continued

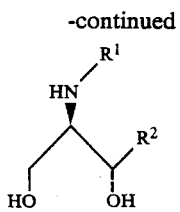 (II)-L in which R¹ and R² are as defined above, or the corresponding racemate, with an organic reagent which is able selectively to react with a primary hydroxyl group, with the formation of compounds of the formula (III)

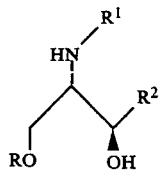 (III)-D

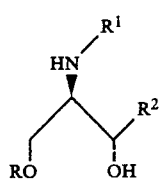 (III)-L in which R denotes a hydroxyl protective group, esterifying the compound of the formula (III) with an organic carboxylic acid with the formation of a compound of the formula (IV)

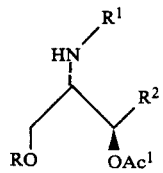 (IV)-D

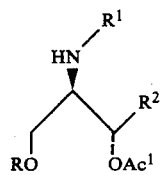 (IV)-L in which Ac¹ denotes the acyl radical or an organic carboxylic acid, removing the hydroxyl protective group R from the compounds of the formula (IV) by acid hydrolysis with the formation of corresponding compounds of the formula (VII)

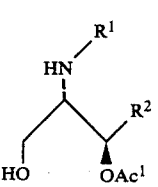 (VII)-D

-continued

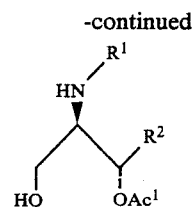 (VII)-L reacting the compound of the formula (VII) with the O-trifluoroacetimidate or O-trichloroacetimidate of a D-glucose whose hydroxyl groups in the 2, 3, 4 and 6 positions are protected by acyl radicals Ac⁴ in the presence of boron trifluoride etherate or trimethylsiloyl trifluoromethanesulfonate, with the formation of compounds of the corresponding formula (X)

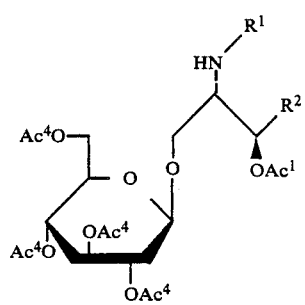 (X)-D

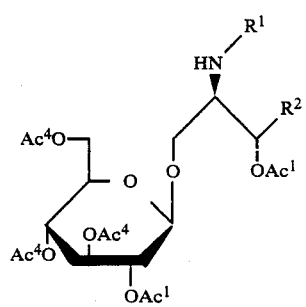 (X)-L separating, if a racemate is used as starting material, into the diastereomers, by chromatography or fractional crystallization, the compound of the formula (X), and eliminating simultaneously the acyl groups Ac¹ and Ac⁴ from the compounds of the formula (X), in each case compounds of the D- or L-series being produced from compounds of the D- or L-series, respectively.

2. A process for the preparation of the sphingosine derivatives of the formula (I)-D or (I)-L

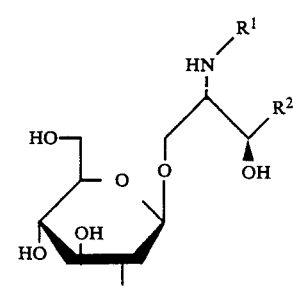 (I)-D

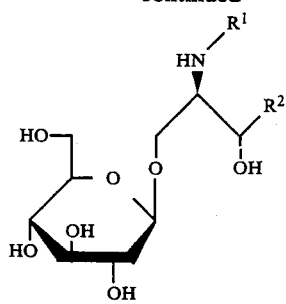 (I)-L in which $R^1$ denotes an acyl radical selected from the group consisting of radicals of fatty acids having 14 or 24 carbon atoms and the corresponding acyl radicals having a hydroxyl group in the α-position or having 1 or 2 double bonds in the cis configuration, and $R^2$ denotes a radical selected from the group consisting of the pentadecanyl and the heptadecanyl radical and the corresponding $C_{15}$ and $C_{17}$ radicals having 1, 2 or 3 double bonds, one of which in each case being located in the 1,2-position and having the trans configuration, the other, or others, when present, having the cis configuration; which comprises reacting a racemic compound of the formula (II)-D and (II)-L

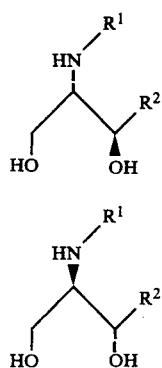 (II)-D

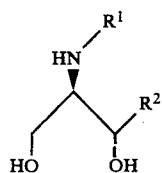 (II)-L in which $R^1$ and $R^2$, are as defined above, with an organic reagent which is able selectively to react with a primary hydroxyl group, with the formation of compounds of the formula (III)

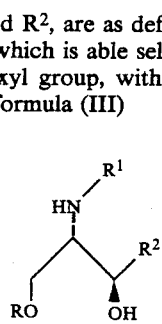 (III)-D

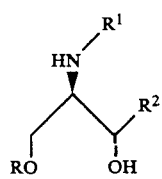 (III)-L in which R denotes a hydroxyl protective group, esterifying the compound of the formula (III) with an optically active organic acid, and separating into the diastereomers, by chromatography or fractional crystallization, the resulting mixture of diastereomeric compounds of the formula (V)

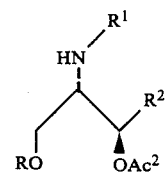 (V)-D

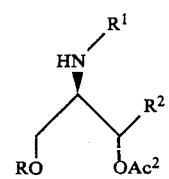 (V)-L in which $Ac^2$ denotes the acyl radical of an optically active organic acid, removing the hydroxyl protective group R from the diastereomers of the formula (V) by acid hydrolysis with the formation of corresponding compounds of the formula (VIII)

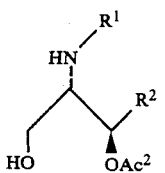 (VIII)-D

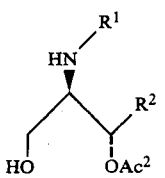 (VIII)-L reacting the compound of the formula (VIII) with the O-trifluoroacetimidate or O-trichloroacetimidate of a D-glucose whose hydroxyl groups in the 2, 3, 4 and 6 positions are protected by acyl radicals $Ac^4$ in the presence of boron trifluoride etherate or trimethylsilyl trifluoromethanesulfonate, with the formation of compounds of the corresponding formula (XI)

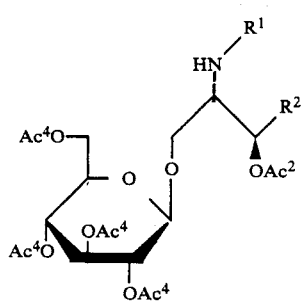 (XI)-D

-continued (XI)-L

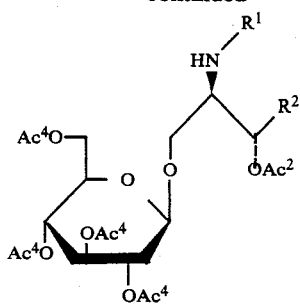

and eliminating simultaneously the acyl groups $Ac^2$ and $Ac^4$ from the compounds of the formula (XI), in each case compounds of the D- or L-series being produced from compounds of the D- L-series respectively.

3. A process for the preparation of the sphingosine derivatives of the formula (I)-D or (I)-L (I)-D

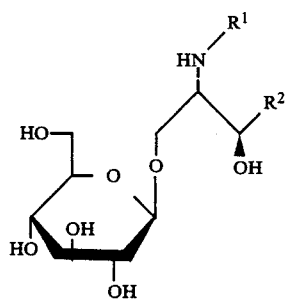

(I)-L

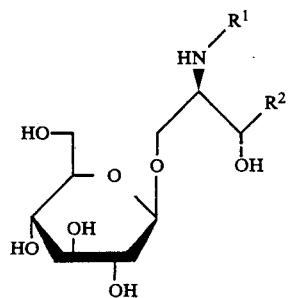

in which $R^1$ denotes an acyl radical selected from the group consisting of radicals of fatty acids having 14 to 24 carbon atoms and the corresponding acyl radicals having a hydroxyl group in the α-position or having 1 or 2 double bonds in the cis configuration and $R^2$ denotes a radical selected from the group consisting of the pentadecanyl and the heptadecanyl radical and the corresponding $C_{15}$ and $C_{17}$ radicals having 1, 2 or 3 double bonds, one of which in each case being located in the 1,2-position and having the trans configuration, the other, or others, when present, having the cis configuration; comprising reacting a racemic compound of the formula (II)-D and (II)-L (II)-D

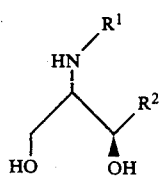

-continued (II)-L

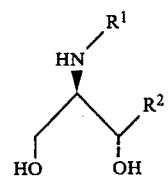

in which $R^1$ and $R^2$ are as defined above, with an organic reagent which is able selectively to react with a primary hydroxyl group, with the formation of compounds of the formula (III)

(III)-D

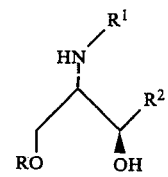

(III)-L

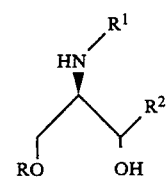

in which R denotes a hydroxyl protective group, esterifying the compound of the formula (III) with an optically active organic acid, and separating into the diastereomers, by chromatography or fractional crystallization, the resulting mixture of diastereomeric compounds of the formula (V)

(V)-D

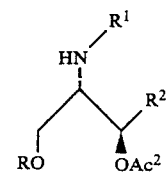

(V)-L

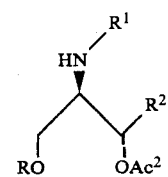

in which $Ac^2$ denotes the acyl radical of an optically active organic acid, deacylating the individual diastereomers of the formula (V) and esterifying with an organic carboxylic acid with the formation of enantiomeric compounds of the formula (VI)

(VI)-D

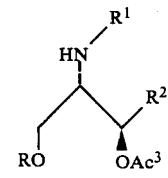

-continued

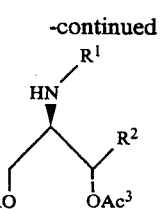
(VI)-L in which $Ac^3$ denotes the acyl radical of an organic carboxylic acid, removing the hydroxyl protective group R from the enantiomers of the formula (VI) by acid hydrolysis with the formation of corresponding compounds of the formula (IX)

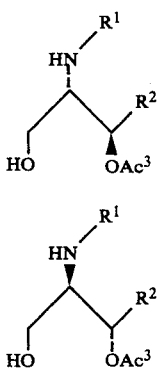
(IX)-D (IX)-L reacting the compound of the formula (IX) with the O-trifluoroacetimidate or O-trichloroacetimidate of a D-glucose whose hydroxyl groups in the 2, 3, 4 and 6 positions are protected by acyl radicals $Ac^4$ in the presence of boron trifluoride etherate or trimethylsilyl trifluoromethanesulfonate, with the formation of compounds of the corresponding formula (XII)

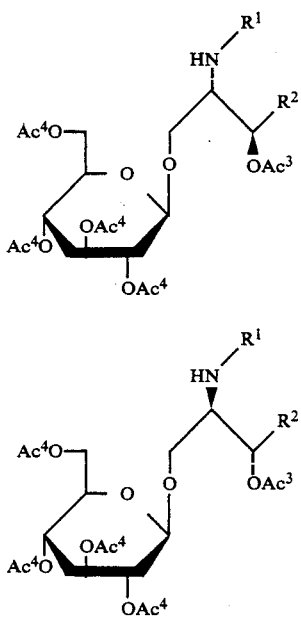
(XII)-D (XII)-L and eliminating simultaneously the acyl groups $Ac^3$ and $Ac^4$ from the compounds of the formula (XII), in each case compounds of the D- or L-series being produced from compounds of the D- or L-series respectively.

4. The process as claimed in claim 1, wherein the acyl radical $Ac^1$ used is that of an aliphatic or aromatic carboxylic acid or a tert.-butoxycarbonyl group.

5. The process as claimed in claim 4, wherein the acyl radical $Ac^1$ is the acyl radical or benzoic acid or a substituted benzoic acid.

6. The process as claimed in claim 1, wherein the hydroxyl protective group R is selected from the group consisting of triphenylmethyl, monomethoxy-triphenylmethyl, tert.-butyl, trichloroacetyl, trimethylsilyl, tert.-butyldimethylosilyl and tert.-butyldiphenylsilyl.

7. The process as claimed in claim 2, wherein the hydroxyl protective group R is selected from the group consisting of triphenylmethyl, monomethoxy-triphenylmethyl, tert.-butyl, trichloroacetyl, trimethylsilyl, tert.-butyldimethylsilyl and tert.-butyldiphenylsilyl.

8. The process as claimed in claim 3, wherein the hydroxyl protective group R is selected from the group consisting of triphenylmethyl, monomethoxy-triphenylmethyl, tert.-butyl, trichloroacetyl, trimethylsilyl, tert.-butyldimethylsilyl and tert.-butylodiphenylsilyl.

9. The process as claimed in claim 3, wherein the acyl radical $Ac^3$ used is that of an aliphatic or aromatic carboxylic acid or a tert.-butoxycarbonyl group.

10. The process as claimed in claim 9, wherein the acyl radical $Ac^3$ is the acyl radical of benzoic acid or a substituted benzoic acid.

11. The process as claimed in claim 2, wherein the acyl radical $Ac^2$ used is that of a readily accessible optically active organic acid, selected from the group consisting of tartaric acid, debenzoyltartaric acid, mandelic acid, O-acetylomandelic acid, camphoric acid, camphorsulfonic acid and bromocamphorsulfonic acid.

12. The process as claimed in claim 1, wherein the acyl radical $Ac^4$ used is that of an aliphatic or aromatic carboxylic acid.

13. The process as claimed in claim 2, wherein the acyl radical $Ac^4$ used is that of an aliphatic or aromatic carboxylic acid.

14. The process as claimed in claim 3, wherein the acyl radical $Ac^4$ used is that of an aliphatic or aromatic carboxylic acid.

15. The process as in claim 12, wherein the acyl radical $Ac^4$ is the acetyl or benzoyl radical.

16. The process as in claim 13, wherein the acyl radical $Ac^4$ is the acetyl or benzoyl radical.

17. The process as in claim 14, wherein the acyl radical $Ac^4$ is the acetyl or benzoyl radical.

18. The process as claimed in claim 1, wherein the elimination of the acyl radicals $Ac^1$ and $Ac^4$ in the last stage of the process is carried out by treatment with an alkali metal alcoholate.

19. The process as claimed in claim 2, wherein the elimination of the acyl radicals $Ac^2$ and $Ac^4$ in the last stage of the process is carried out by treatment with an alkali metal alcoholate.

20. The process as claimed in claim 3, wherein the elimination of the acyl radicals $AC^3$ and $Ac^4$ in the last stage of the process is carried out by treatment with an alkali metal alcoholate.

21. The process as claim in claim 1, wherein the reaction with the trifluoroacetimidate or trichloroacetimidate is carried out in an anhydrous polar solvent.

22. The process as in claim 2, wherein the reaction with the trifluoroacetimidate or trichloroacetimidate is carried out in an anhydrous polar solvent.

23. The process as in claim 3, wherein the reaction with the trifluoroacetimidate or trichloroacetimidate is carried out in an anhydrous polar solvent.

* * * * *